United States Patent
Okuma et al.

(10) Patent No.: US 10,435,680 B2
(45) Date of Patent: Oct. 8, 2019

(54) THERMOSTABLE CELLOBIOHYDROLASE

(71) Applicant: HONDA MOTOR CO., LTD., Minato-Ku, Tokyo (JP)

(72) Inventors: Jiro Okuma, Wako (JP); Yoshitsugu Hirose, Wako (JP); Migiwa Suda, Kisarazu (JP); Asuka Yamaguchi, Tokyo (JP); Yasuhiro Kondo, Kawagoe (JP); Masaru Sato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 15/467,542

(22) Filed: Mar. 23, 2017

(65) Prior Publication Data

US 2017/0275606 A1 Sep. 28, 2017

(30) Foreign Application Priority Data

Mar. 28, 2016 (JP) ................................ 2016-064519

(51) Int. Cl.
| C12P 19/02 | (2006.01) |
| C12N 9/42  | (2006.01) |
| C12P 19/14 | (2006.01) |
| C12P 19/12 | (2006.01) |

(52) U.S. Cl.
CPC ............ *C12N 9/2437* (2013.01); *C12P 19/02* (2013.01); *C12P 19/12* (2013.01); *C12P 19/14* (2013.01); *C12Y 302/01004* (2013.01); *C12Y 302/01091* (2013.01); *Y02E 50/16* (2013.01)

(58) Field of Classification Search
None
See application file for complete search history.

(56) References Cited

U.S. PATENT DOCUMENTS

| 7,785,854 B2 * | 8/2010 | St-Pierre ........ C12Y 302/01091 435/183 |
| 2015/0259659 A1 | 9/2015 | Suda et al. |
| 2015/0259660 A1 | 9/2015 | Okuma et al. |
| 2016/0053246 A1 | 2/2016 | Suda et al. |

FOREIGN PATENT DOCUMENTS

WO 2014/157492 A1 10/2014

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Extended European search report issued over the corresponding EP Patent Application 17162735.9 dated May 18, 2017.
Bolam et al., "Pseudomonas cellulose-binding domains mediate their effects by increasing enzyme substrate proximity", Biochem. J., 1998, vol. 331, p. 775-781.
N. Din et al., "C1-Cx revisited: Intramolecular synergism in a cellulase", Proc. Natl. Acad. Sci. USA, 1994, vol. 91, p. 11383-11387.
K. Riedel et al., "The modular cellulase CelZ of the thermophilic bacterium Clostridium stercorarium contains a thermostabilizing domain", FEMS Microbiology Letters, 1998, vol. 164, p. 261-267.

\* cited by examiner

*Primary Examiner* — Richard G Hutson

(74) *Attorney, Agent, or Firm* — Carrier Blackman & Associates, P.C.; Joseph P. Carrier; Fulchand P. Shende

(57) ABSTRACT

A thermostable cellobiohydrolase, having a cellulose-binding motif domain including (A1) a polypeptide including an amino acid sequence represented by SEQ ID NO: 1, (B1) a polypeptide including an amino acid sequence in which at least one amino acid has been deleted, substituted, or added in the amino acid sequence represented by SEQ ID NO: 1, and having a cellulose-binding function, or (C1) a polypeptide including an amino acid sequence having 70% or greater sequence identity with the amino acid sequence represented by SEQ ID NO: 1, and having a cellulose-binding function, and also having a cellobiohydrolase catalytic domain, wherein the thermostable cellobiohydrolase exhibits hydrolysis activity against a substrate of phosphoric acid swollen Avicel at least under conditions of 95° C. and pH 5.5.

1 Claim, 5 Drawing Sheets

Specification includes a Sequence Listing.

FIG. 1

```
AR19G-166c4A      1 ACQVSRYAVAQNPEGGATVAVEFTNTSSPHIGTIEIDEPNPSQJTDLMNGSYQTGQVTVTIAAWGTIPAGSSVTEGFNVSNSGSI  90
Microbispora CBM2 1 -GQVTVLYNQNDGGFGTNVTFSIL-GDPVNGRITSEP-AGQTVQLNGTVDSCQVTVVASYVAEDTGSTNGENGSNVGSI        87

AR19G-166c4A      91 PAPSSFTIGPGGTAGGGPQPTPTPTRTPTPAAPTATPPVAPTATPTRTPTPTLTSTPGPTPPPSGTIHLDNPFIGAIGYVNPDWA 180
Microbispora CBM2 88 PAPSSF4LGVTE--------------------------------------------------------------------------- 100

AR19G-166c4A      181 TNVISQANQTADPTLAAQMRKVATYSTAWMLDRIAATTAGRGLRGHLDEALRQMQQAGQPVVITLVTYDLPNRDCSAAASNGELLVAQNG 270
Microbispora CBM2 100 ----------------------------------------------------------------------------------------- 100

AR19G-166c4A      271 LARYKAEFIDPIVAILSDPRYAGLRIVTIIEPDSLPNLVTNLSIPACAEAQNAYIEGIRYAVNRLRTIPNVYTYLDIAHSGWLGWDNVNFN 360
Microbispora CBM2 100 ----------------------------------------------------------------------------------------- 100

AR19G-166c4A      361 GAVANLVTQVVQGMDQGFNSIDGFITNVANYPLEEPYLPDDPNLITAGQPVRSASFYEWNPYFDELDYALALRNAFIGRGFPSTIGMLIDT 450
Microbispora CBM2 100 ----------------------------------------------------------------------------------------- 100

AR19G-166c4A      451 SRNGWMGGCSYGQCRPTGPSSDTSSVWAYVDGSRVDRRYHRGWMCNQAGGIGERPQAAPRSGIDAYVWVKPPGEESDGVSQPGIVDPDDPNK 540
Microbispora CBM2 100 ----------------------------------------------------------------------------------------- 100

AR19G-166c4A      541 KFDPMCDPNGQSRYVNSAYPTGALPNAPHAGRWFPQQFEILVRNAYPPIQP 590
Microbispora CBM2 100 --------------------------------------------------- 100
```

THERMOSTABLE CELLOBIOHYDROLASE

TECHNICAL FIELD

The present invention relates to a thermostable cellobiohydrolase, a polynucleotide encoding the thermostable cellobiohydrolase, an expression vector for expressing the thermostable cellobiohydrolase, a transformant into which the expression vector has been incorporated, and a method for producing a cellulose degradation product using the thermostable cellobiohydrolase.

Priority is claimed on Japanese Unpublished Patent Application No. 2016-064519, filed Mar. 28, 2016, the content of which is incorporated herein by reference.

BACKGROUND ART

In recent years, as a result of environmental problems such as global warming and atmospheric pollution, as well as concerns related to energy supplies for transportation, including the dramatic increase in the cost of crude oil and the expectation of a depletion in crude oil sources in the near future (peak oil), the development of alternative energy sources to oil has become an extremely important issue. Plant biomass or lignocellulose is the most plentiful renewable energy source on earth, and holds great promise as an alternative energy source to oil. The main component of plant biomass dry weight is lignocellulose, which is composed of polysaccharides such as cellulose and hemicellulose, and lignin. For example, polysaccharides can be hydrolyzed by a glycoside hydrolase such as a cellulase or hemicellulase to form monosaccharides such as glucose and xylose, which can then be used as biofuels or the raw materials for chemical products.

Lignocellulose is recalcitrant due to its highly complex structure, and is difficult to degrade or hydrolyze with a single glycoside hydrolase. The complete degradation of lignocellulose generally requires three types of enzymes, namely an endoglucanase (cellulase or endo-1,4-(3-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21), and it is thought that the addition of a further plurality of enzymes including the hemicellulase xylanase (endo-1,4-β-xylanase, EC 3.2.1.8) and other plant cell wall-degrading enzymes such as β-xylosidase (EC 3.2.1.37) is also necessary.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 65° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. Another advantage is that by performing the reaction at high temperature, proliferation of unwanted bacteria during the enzyme reaction can be prevented. As a result, for all of the various glycoside hydrolases, the development of enzymes having superior thermal stability is very desirable.

Cellulases that function in high-temperature environments have conventionally been isolated from thermophilic filamentous fungi and thermophilic bacteria and the like, but the majority of these cellulases are enzymes having endoglucanase activity, xylanase activity, xylosidase activity or glucosidase activity, and very few cellobiohydrolases, which play an important role in lignocellulose hydrolysis processes, have been isolated. However, in terms of cellobiohydrolases which initiate hydrolysis from the non-reducing ends of cellulose, a cellobiohydrolase of the GH6 family having an optimum temperature exceeding 75° C. has been reported (for example, see Patent Document 1).

Among cellobiohydrolases, there are some enzymes which are composed of not only the catalytic domain that hydrolyzes cellulose, but also have a module that has the function of binding cellulose (hereafter sometimes referred to as a "carbohydrate-binding module" or CBM). Although the CBM itself exhibits no degradation activity, the CBM by itself has the ability to bind to cellulose. Known functions of CBMs include increasing the concentration of the catalytic domain in the vicinity of the substrate by adsorbing to the insoluble substrate, thereby increasing the cellulose degradation rate, and severing hydrogen bonding between cellulose chains through CBM binding, thereby destroying crystal structures (Non-Patent Documents 1 and 2). Further, if a CBM is removed from a cellobiohydrolase which degrades crystalline cellulose, then although the reactivity relative to soluble substrates does not change, the degradation activity and affinity relative to crystalline cellulose decrease dramatically, and therefore it is thought that the CBM is a domain that is required for the enzyme to act upon crystalline cellulose (Non-Patent Document 3).

PRIOR ART LITERATURE

Patent Documents

Patent Document 1: International Patent Publication No. 2014/157492

Non-Patent Documents

Non-patent document 1: Bolam et al., Biochemical Journal, 1998, vol. 331, pp. 775-781.
Non-patent document 2: DIN et al., Proceedings of the National Academy of Sciences USA, 1994, vol. 91, pp. 11383-11387.
Non-patent document 3: Riedel et al., FEMS Microbiology Letters, 1998, vol. 164, pp. 261-267.

SUMMARY OF THE INVENTION

Problems to be Solved by the Invention

The present invention has an object of providing a thermostable cellobiohydrolase having a novel CBM, the cellobiohydrolase exhibiting cellobiohydrolase activity at least at 95° C., and at 105° C. in the presence of calcium ions, as well as providing a polynucleotide encoding a thermostable cellobiohydrolase having the above CBM, an expression vector for expressing the thermostable cellobiohydrolase, a transformant into which the expression vector has been incorporated, and a method for producing a cellulose degradation product using the thermostable cellobiohydrolase.

Means for Solving the Problem

In order to achieve the above object, the inventors of the present invention extracted DNA directly from the high-temperature soils of hot springs, and by carrying out large-scale metagenomic sequencing of the microbial flora that was difficult to culture, they succeeded in obtaining a thermostable cellobiohydrolase having a novel amino acid sequence, thus enabling them to complete the present invention.

In other words, a thermostable cellobiohydrolase, a polynucleotide, an expression vector, a transformant, a method for producing a thermostable cellobiohydrolase, a cellulase mixture, and a method for producing a cellulose degradation product according to the present invention have the aspects [1] to [12] described below.

[1] A thermostable cellobiohydrolase,
  having a cellulose-binding motif domain including:
    (A1) a polypeptide including an amino acid sequence represented by SEQ ID NO: 1,
    (B1) a polypeptide including an amino acid sequence in which at least one amino acid has been deleted, substituted, or added in the amino acid sequence represented by SEQ ID NO: 1, and having a cellulose-binding function, or
    (C1) a polypeptide including an amino acid sequence having 70% or greater sequence identity with the amino acid sequence represented by SEQ ID NO: 1, and having a cellulose-binding function, and
  also having a cellobiohydrolase catalytic domain, wherein
  the thermostable cellobiohydrolase exhibits hydrolysis activity against a substrate of phosphoric acid swollen Avicel at least under conditions of 95° C. and pH 5.5.

[2] The thermostable cellobiohydrolase according to [1], wherein the cellobiohydrolase catalytic domain includes:
  (A2) a polypeptide including a partial sequence from the leucine residue at position 164 to the proline residue at position 590 of the amino acid sequence represented by SEQ ID NO: 3,
  (B2) a polypeptide including an amino acid sequence in which at least one amino acid has been deleted, substituted, or added in the partial sequence from the leucine residue at position 164 to the proline residue at position 590 of the amino acid sequence represented by SEQ ID NO: 3, and having hydrolysis activity against a substrate of phosphoric acid swollen Avicel at least under conditions of 95° C. and pH 5.5, or
  (C2) a polypeptide including an amino acid sequence having 70% or greater sequence identity with the partial sequence from the leucine residue at position 164 to the proline residue at position 590 of the amino acid sequence represented by SEQ ID NO: 3, and having hydrolysis activity against a substrate of phosphoric acid swollen Avicel at least under conditions of 95° C. and pH 5.5.

[3] The thermostable cellobiohydrolase according to [1], including:
  (A3) a polypeptide including the amino acid sequence represented by SEQ ID NO: 3,
  (B3) a polypeptide including an amino acid sequence in which at least one amino acid has been deleted, substituted, or added in the amino acid sequence represented by SEQ ID NO: 3, and having hydrolysis activity against a substrate of phosphoric acid swollen Avicel at least under conditions of 95° C. and pH 5.5, or
  (C3) a polypeptide including an amino acid sequence having 70% or greater sequence identity with the amino acid sequence represented by SEQ ID NO: 3, and having hydrolysis activity against a substrate of phosphoric acid swollen Avicel at least under conditions of 95° C. and pH 5.5.

[4] The thermostable cellobiohydrolase according to any one of [1] to [3] which, in the presence of calcium ions, exhibits hydrolysis activity against a substrate of phosphoric acid swollen Avicel at least under conditions of 105° C. and pH 5.5.

[5] A polynucleotide, having
  (a1) a nucleotide sequence encoding a polypeptide including the amino acid sequence represented by SEQ ID NO: 1,
  (b1) a nucleotide sequence encoding a polypeptide including an amino acid sequence in which at least one amino acid has been deleted, substituted, or added in the amino acid sequence represented by SEQ ID NO: 1, the polypeptide having a cellulose-binding function,
  (c1) a nucleotide sequence encoding a polypeptide including an amino acid sequence having 70% or greater sequence identity with the amino acid sequence represented by SEQ ID NO: 1, the polypeptide having a cellulose-binding function,
  (d1) a nucleotide sequence having 80% or greater sequence identity with a nucleotide sequence represented by SEQ ID NO: 2, and encoding a polypeptide having a cellulose-binding function, or
  (e1) a nucleotide sequence of a polynucleotide which hybridizes under stringent conditions with a polynucleotide including the nucleotide sequence represented by SEQ ID NO: 2, the nucleotide sequence encoding a polypeptide having a cellulose-binding function,
  and also having a nucleotide sequence encoding a polypeptide having cellobiohydrolase catalytic activity.

[6] The polynucleotide according to [5], including:
  (a2) a nucleotide sequence encoding a polypeptide including the amino acid sequence represented by SEQ ID NO: 3,
  (b2) a nucleotide sequence encoding a polypeptide including an amino acid sequence in which at least one amino acid has been deleted, substituted, or added in the amino acid sequence represented by SEQ ID NO: 3, the polypeptide having hydrolysis activity against a substrate of phosphoric acid swollen Avicel at least under conditions of 95° C. and pH 5.5,
  (c2) a nucleotide sequence encoding a polypeptide including an amino acid sequence having 70% or greater sequence identity with the amino acid sequence represented by SEQ ID NO: 3, the polypeptide having hydrolysis activity against a substrate of phosphoric acid swollen Avicel at least under conditions of 95° C. and pH 5.5,
  (d2) a nucleotide sequence having 80% or greater sequence identity with a nucleotide sequence represented by SEQ ID NO: 4, and encoding a polypeptide having hydrolysis activity against a substrate of phosphoric acid swollen Avicel at least under conditions of 95° C. and pH 5.5, or
  (e2) a nucleotide sequence of a polynucleotide which hybridizes under stringent conditions with a polynucleotide including the nucleotide sequence represented by SEQ ID NO: 4, the nucleotide sequence encoding a polypeptide having hydrolysis activity against a substrate of phosphoric acid swollen Avicel at least under conditions of 95° C. and pH 5.5.

[7] The polynucleotide according to [5] or [6], wherein the polypeptide also exhibits, in the presence of calcium ions, hydrolysis activity against a substrate of phosphoric acid swollen Avicel at least under conditions of 105° C. and pH 5.5.

[8] An expression vector incorporating the polynucleotide according to any one of [5] to [7], the expression vector being capable of expressing a polypeptide having cellobiohydrolase activity in a host cell.

[9] A transformant into which the expression vector according to [8] has been introduced.

[10] A method for producing a thermostable cellobiohydrolase, the method including generating the thermostable cellobiohydrolase in the transformant according to [8].

[11] A glycoside hydrolase mixture, including the thermostable cellobiohydrolase according to any one of [1] to [4], a thermostable cellobiohydrolase encoded by the polynucleotide according to any one of [5] or [7], or a thermostable cellobiohydrolase produced by the method for producing a thermostable cellobiohydrolase according to [10], and at least one other glycoside hydrolase.

[12] A method for producing a cellulose degradation product, the method including generating the cellulose degradation product by bringing a material containing cellulose into contact with the thermostable cellobiohydrolase according to any one of [1] to [4], a thermostable cellobiohydrolase encoded by the polynucleotide according to any one of [5] or [7], the transformant according to [8], a thermostable cellobiohydrolase produced by the method for producing a thermostable cellobiohydrolase according to [10], or the glycoside hydrolase mixture according to [11].

Effects of the Invention

The thermostable cellobiohydrolase according to the present invention has cellobiohydrolase activity at least at 95° C. and pH 5.5, and at least at 105° C. and pH 5.5 in the presence of calcium ions. Accordingly, the thermostable cellobiohydrolase is suitable for hydrolysis processes of materials containing cellulose under high-temperature conditions.

Furthermore, the polynucleotide according to the present invention, an expression vector incorporating the polynucleotide, and a transformant into which the expression vector has been introduced can be used favorably in the production of the thermostable cellobiohydrolase according to the present invention.

BRIEF DESCRIPTION OF THE DRAWINGS

FIG. 1 is an alignment diagram of the amino acid sequence (SEQ ID NO: 3) of a polypeptide presumed to be encoded by an open reading frame AR19G-166c4A and the amino acid sequence of the CBM2 domain of an α-L-arabinofuranosidase of an *Actinomyces Microbispora* subspecies.

FIG. 2 is a diagram showing the SDS-PAGE analysis results of the AR19G-166c4A-19-2 protein obtained by expressing the AR19G-166c4A-19-2 gene in *E. coli* in Example 1, wherein FIG. 2(A) illustrates the results of CBB staining, and FIG. 2(B) illustrates the results of Western blotting.

FIG. 5(A) shows actual measurement data of the change in the fluorescence intensity of SYPRO Orange that is generated in association with the thermal denaturation, either in the presence of calcium ions or in the absence of calcium ions, exhibited by the AR19G-166c4A-19-2 protein obtained by expressing the AR19G-166c4A-19-2 gene in *E. coli* and the AR19G-166-QA protein obtained by expressing the AR19G-166-QA gene in *E. coli* in Example 1. FIG. 5(B) shows a first derivative "−d(Fluorescence)/dt" of the fluorescence intensity change curve of the diagram (A).

DETAILED DESCRIPTION OF THE INVENTION

[Thermostable Cellobiohydrolase]

Figure 2:
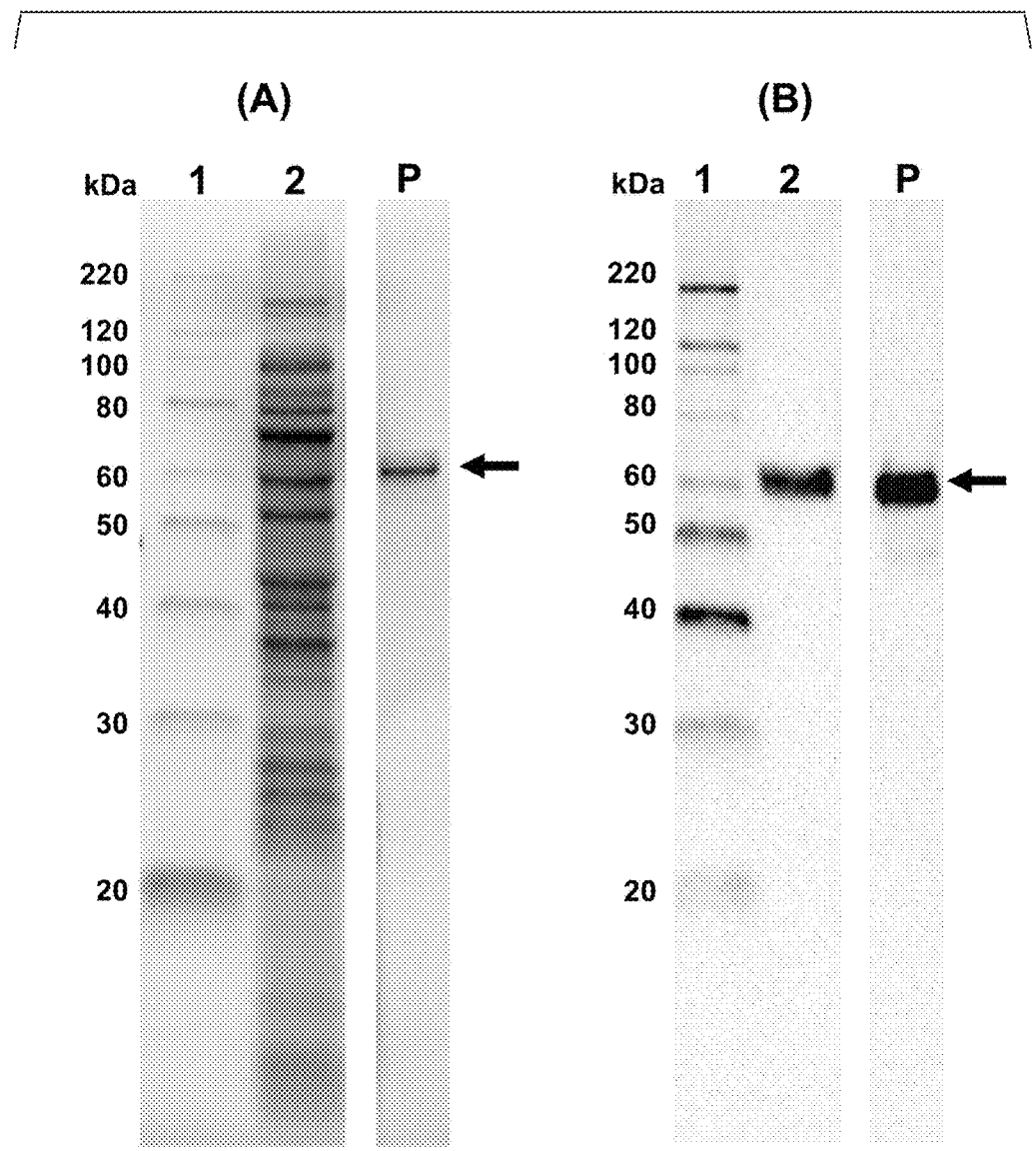

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that using current culturing techniques that target the isolation of microorganisms, a mere 0.1% or less of the microorganisms that exist in natural samples extracted from the natural world have been able to be isolated. This difficulty in culturing microorganisms is one of the reasons hindering the development of thermostable cellobiohydrolases. Accordingly, the development of thermostable cellobiohydrolases requires an approach that does not rely on conventional isolation and culturing techniques.

In recent years, as a result of the development of next generation sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA of microbial groups from high-temperature hot spring soils (for example, hot spring water of 58 to 78° C. containing soil, mud, biomat and biofilm and the like) collected from locations in Japan, and conducted shotgun sequencing and annotation of the genomic DNA, thus obtaining open reading frames (ORFs) having amino acid sequences similar to those of known cellobiohydrolases. Primers were then designed based on the nucleotide sequence information of the obtained ORFs, and gene candidates were cloned by the PCR method from the genomic DNA derived from the high-temperature hot spring soils. The PCR-cloned DNAs were incorporated into *E. coli*, and proteins encoded by these nucleotide sequences were expressed and subjected to functional screening by phosphoric acid swollen Avicel (hereafter often abbreviated as PSA) degradation activity assay. Finally, a thermostable cellobiohydrolase (hereafter also referred to as "AR19G-166c4A-19-2") having PSA degradation activity was obtained from these ORFs. The amino acid sequence of AR19G-166c4A-19-2 is represented by SEQ ID NO: 3, and the nucleotide sequence encoding the amino acid sequence of AR19G-166c4A-19-2 is represented by SEQ ID NO: 4.

AR19G-166c4A-19-2 has a cellobiohydrolase catalytic domain and a cellulose-binding module (hereafter often abbreviated as CBM). Within the amino acid sequence represented by SEQ ID NO: 3, the 102 amino acid residues from the cysteine residue at position 2 through to the cysteine residue at position 103 is the CBM domain, and the 427 amino acid residues from the leucine residue at position 164 through to the proline residue at position 590 is the cellobiohydrolase catalytic domain. The amino acid sequence of the CBM domain of AR19G-166c4A-19-2 is represented by SEQ ID NO: 1, and the nucleotide sequence encoding the amino acid sequence of the CBM domain of AR19G-166c4A-19-2 is represented by SEQ ID NO: 2. In other words, AR19G-166c4A-19-2 is a glycoside hydrolase having cellobiohydrolase activity.

In the present description, the expression "cellobiohydrolase activity" means activity which generates cellobiose by hydrolysis from the non-reducing end of a substrate containing at least one compound selected from the group consisting of compounds composed of β-1,3 linkages and β-1,4 linkages and crystalline cellulose, or PSA. Examples of the "compounds composed of β-1,3 linkages and β-1,4 linkages" include glucans composed of 0-1,3 linkages and 0-1,4 linkages and oligosaccharides composed of β-1,3 linkages and β-1,4 linkages.

Further, in the present description, the expression "has activity" or "exhibits activity" means that the enzyme acts against at least one substrate, with a significant difference occurring in the amount of reducing ends or the color development reaction of the hydrolyzed substrate compared with a negative control.

Accordingly, the expression "has cellobiohydrolase activity" means that the enzyme acts against a substrate of PSA or at least one compound selected from the group consisting of compounds composed of β-1,3 linkages and β-1,4 linkages and crystalline cellulose, and generates a significant difference in the amount of reducing ends or the color development reaction of the hydrolyzed substrate compared with a negative control.

Although the CBM itself exhibits no degradation activity, the CBM by itself has the ability to bind to cellulose. Known functions of CBMs include increasing the concentration of the catalytic domain in the vicinity of the substrate by adsorbing to the insoluble substrate, thereby increasing the cellulose degradation rate, and severing hydrogen bonding between cellulose chains through CBM binding, thereby destroying crystal structures.

When the amino acid sequence of AR19G-166c4A-19-2 was searched against a database of known amino acid sequences, the cellobiohydrolase catalytic domain was found to be identical with the amino acid sequence (SEQ ID NO: 10) of AR19G-166-QA, which is a one-amino acid mutant (R299Q) of AR19G-166RA disclosed in Patent Document 1. Further, the amino acid sequence of the CBM exhibited the highest sequence identity with the CBM (carbohydrate-binding module) 2 domain of an α-L-arabinofuranosidase of an *Actinomyces Microbispora* subspecies (Genbank registration ID: ETK36906.1) (SEQ ID NO: 9), with a sequence identity (homology) between the two sequences of 64%.

Because AR19G-166c4A-19-2 has the same cellobiohydrolase catalytic domain as the one-amino acid mutant (R299Q) of AR19G-166RA, AR19G-166c4A-19-2 exhibits similar activity to AR19G-166RA and AR19G-166QV, with high hydrolysis activity against PSA, and weak hydrolysis activity against lichenan composed of glucans having β-1,3 linkages and β-1,4 linkages, and the crystalline cellulose Avicel. On the other hand, AR19G-166c4A-19-2 exhibits almost no hydrolysis activity against carboxymethyl cellulose (hereafter sometimes abbreviated as CMC) or laminarin composed of glucans having β-1,3 linkages and β-1,6 linkages.

AR19G-166c4A-19-2 has cellobiohydrolase activity at least under conditions of 95° C. and pH 5.5. Actually, as shown below in Example 1, at a pH of 5.5, AR19G-166c4A-19-2 exhibits PSA hydrolysis activity across a broad temperature range from 50 to 105° C., and also exhibits Avicel hydrolysis activity across a broad temperature range from 50 to 99° C.

Further, in the presence of divalent metal ions, AR19G-166c4A-19-2 exhibits even higher cellobiohydrolase activity at high temperatures than those observed in the absence of such metal ions. Actually, as shown below in Example 1, in the presence of calcium ions, AR19G-166c4A-19-2 exhibits higher cellobiohydrolase activity than that observed in the absence of calcium ions at temperatures of 75° C. or higher. In particular, in the presence of calcium ions, AR19G-166c4A-19-2 has PSA hydrolysis activity at least under conditions of 105° C. and pH 5.5.

Generally, in a protein having some form of bioactivity, one or more amino acids can be deleted, substituted, or added, without impairing the bioactivity. In other words, in AR19G-166c4A-19-2, one or more amino acids can be deleted, substituted, or added without impairing the cellobiohydrolase activity.

Hence, the thermostable cellobiohydrolase according to the present invention has a CBM including any of the following (A1) to (C1) and a cellobiohydrolase catalytic domain, and exhibits hydrolysis activity against a substrate of phosphoric acid swollen Avicel at least under conditions of 95° C. and pH 5.5. Because the thermostable cellobiohydrolase according to the present invention has a CBM, it exhibits higher cellobiohydrolase activity than thermostable cellobiohydrolases composed solely of a cellobiohydrolase catalytic domain.

(A1) A polypeptide including an amino acid sequence represented by SEQ ID NO: 1, (B1) a polypeptide including an amino acid sequence in which at least one amino acid has been deleted, substituted, or added in the amino acid sequence represented by SEQ ID NO: 1, and having a cellulose-binding function, or (C1) a polypeptide including an amino acid sequence having 70% or greater sequence identity with the amino acid sequence represented by SEQ ID NO: 1, and having a cellulose-binding function.

There are no particular limitations on the cellobiohydrolase catalytic domain of the thermostable cellobiohydrolase according to the present invention, provided it exhibits hydrolysis activity against a substrate of phosphoric acid swollen Avicel at least under conditions of 95° C. and pH 5.5 when linked with the CBM according to the present invention (namely, the CBM including any of (A1) to (C1)), and the catalytic domain may be selected from known thermostable cellobiohydrolases.

The cellobiohydrolase catalytic domain of the thermostable cellobiohydrolase according to the present invention is preferably one of the following (A2) to (C2).

(A2) A polypeptide including a partial sequence from the leucine residue at position 164 to the proline residue at position 590 of the amino acid sequence represented by SEQ ID NO: 3, (B2) a polypeptide including an amino acid sequence in which at least one amino acid has been deleted, substituted, or added in the partial sequence from the leucine residue at position 164 to the proline residue at position 590 of the amino acid sequence represented by SEQ ID NO: 3, and having hydrolysis activity against a substrate of phosphoric acid swollen Avicel at least under conditions of 95° C. and pH 5.5, or (C2) a polypeptide including an amino acid sequence having 70% or greater sequence identity with the partial sequence from the leucine residue at position 164 to the proline residue at position 590 of the amino acid sequence represented by SEQ ID NO: 3, and having hydrolysis activity against a substrate of phosphoric acid swollen Avicel at least under conditions of 95° C. and pH 5.5.

The CBM and the cellobiohydrolase catalytic domain of the thermostable cellobiohydrolase according to the present invention may be either bonded directly or bonded via a linker composed of at least one amino acid residue. Further, the CBM and the cellobiohydrolase catalytic domain may be linked with the CBM positioned at either the N-terminal side or the C-terminal side.

Examples of the thermostable cellobiohydrolase according to the present invention include polypeptides composed of any of the following (A3) to (C3), or polypeptides including any of (A3) to (C3).

(A3) A polypeptide including the amino acid sequence represented by SEQ ID NO: 3, (B3) a polypeptide including an amino acid sequence in which at least one amino acid has been deleted, substituted, or added in the amino acid sequence represented by SEQ ID NO: 3, and having hydrolysis activity against a substrate of phosphoric acid swollen Avicel at least under conditions of 95° C. and pH 5.5, or (C3) a polypeptide including an amino acid sequence having 70% or greater sequence identity with the amino acid sequence represented by SEQ ID NO: 3, and having hydrolysis activity against a substrate of phosphoric acid swollen Avicel at least under conditions of 95° C. and pH 5.5.

In the above polypeptides of (B1), (B2) and (B3), the number of amino acids deleted, substituted, or added in the amino acid sequence represented by SEQ ID NO: 1 or SEQ ID NO: 3 is preferably 1 to 20, more preferably 1 to 10, and still more preferably 1 to 5.

In the above polypeptides of (C1), (C2) and (C3), the sequence identity with the amino acid sequence represented by SEQ ID NO: 1 or SEQ ID NO: 3 is not specifically limited as long as it is 70% or greater but less than 100%, but the sequence identity is preferably 80% or greater but less than 100%, more preferably 85% or greater but less than 100%, still more preferably 90% or greater but less than 100%, and most preferably 95% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity values between amino acid sequences in the present invention were obtained by calculation on the basis of an alignment obtained from the publicly known homology search software BLASTP.

The aforementioned polypeptides of (B1) to (B3) and (C1) to (C3) may be artificially designed, or may be homologs of AR19G-166c4A-19-2 or the like, or partial proteins thereof.

Each of the aforementioned polypeptides of (A1) to (A3), (B1) to (B3) and (C1) to (C3) may be chemically synthesized based on the amino acid sequence, or may be generated by a protein expression system using a polynucleotide according to the present invention described below. Further, each of the polypeptides of (B1) to (B3) and (C1) to (C3) can also be artificially synthesized based on the polypeptide including the amino acid sequence represented by SEQ ID NO: 1 or SEQ ID NO: 3, by using a gene recombination technique to introduce one or more amino acid mutations.

The thermostable cellobiohydrolase according to the present invention acts against PSA as a substrate. The thermostable cellobiohydrolase may also act against other β-glucans or oligosaccharides besides PSA as substrates. Examples of these other β-glucans or oligosaccharides include crystalline celluloses such as Avicel, bacterial microcrystalline cellulose (hereafter sometimes abbreviated as BMCC) and filter paper; CMC; oligosaccharides composed of β-1,4 linkages such as cellobiose; xylan; p-nitrophenyl-β-D-galactopyranoside (hereafter sometimes abbreviated as PNPGAL); p-nitrophenyl-β-D-xylopyranoside (hereafter sometimes abbreviated as PNPX); glucans composed of β-1,3 and β-1,4 linkages such as lichenan; glucans composed of β-1,3 and β-1,6 linkages such as laminarin; glucans composed of β-1,3 linkages; glucans composed of β-1,6 linkages; and oligosaccharides composed of β-1,6 linkages such as gentiobiose. The thermostable cellobiohydrolase according to the present invention preferably acts against Avicel and lichenan substrates in addition to PSA.

The thermostable cellobiohydrolase according to the present invention exhibits hydrolysis activity against a PSA substrate, at least under conditions of pH 5.5, preferably within a temperature range from 70 to 100° C., more preferably within a temperature range from 70 to 105° C., and still more preferably within a temperature range from 50 to 105° C. The optimum temperature of the thermostable cellobiohydrolase according to the present invention is preferably within a range from 85 to 100° C., and more preferably within a range from 90 to 100° C.

The thermostable cellobiohydrolase according to the present invention preferably exhibits cellobiohydrolase activity at least within a pH range from pH 4.5 to 6.0, and more preferably exhibits cellobiohydrolase activity within a pH range from pH 4.0 to 6.5.

Further, in the presence of divalent metal ions, the thermostable cellobiohydrolase according to the present invention preferably exhibits higher cellobiohydrolase activity at even higher temperatures than those observed in the absence of such metal ions. In the presence of divalent metal ions, the thermostable cellobiohydrolase according to the present invention preferably has cellobiohydrolase activity at least across a temperature range from 80 to 100° C. and within a pH range from 4.5 to 5.0, more preferably exhibits cellobiohydrolase activity across a temperature range from 80 to 105° C., and across a pH range from 4.5 to 6.5, and still more preferably exhibits cellobiohydrolase activity across a temperature range from 50 to 105° C., and across a pH range from 4.5 to 6.5.

The term "thermostable" used in relation to the thermostable cellobiohydrolase according to the present invention means, for example, that the cellobiohydrolase has cellobiohydrolase activity within a temperature range from 50 to 105° C.

The thermostable cellobiohydrolase according to the present invention may also have other cellulose hydrolysis activity besides the cellobiohydrolase activity. Examples of this other cellulose hydrolysis activity include xylanase activity, β-galactosidase activity, endoglucanase activity, xylosidase activity or β-glucosidase activity.

The thermostable cellobiohydrolase according to the present invention may be an enzyme composed solely of the CBM according to the present invention and the thermostable cellobiohydrolase catalytic domain, or may be an enzyme that also includes other domains. Examples of these other domains include other domains of conventionally known cellobiohydrolases besides the cellobiohydrolase catalytic domain.

For example, the thermostable cellobiohydrolase according to the present invention also includes enzymes obtained by substituting the cellobiohydrolase catalytic domain in a publicly known cellobiohydrolase with any of the aforementioned polypeptides of (A3) to (C3), and enzymes obtained by adding any of the aforementioned polypeptides of (A1) to (C1) to a conventional cellobiohydrolase.

The thermostable cellobiohydrolase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence.

Furthermore, the thermostable cellobiohydrolase according to the present invention may also have various types of tags added, for example at the N-terminal or the C-terminal, so as to facilitate easy purification in the case of generation using an expression system. Examples of tags that may be used include the types of tags widely used in the expression or purification of recombinant proteins, such as His tags, HA (hemagglutinin) tags, Myc tags and Flag tags.

In other words, one aspect of the thermostable cellobiohydrolase according to the present invention contains any of the aforementioned polypeptides of (A3) to (C3); and also contains, according to need, at least one moiety selected from the group consisting of signal peptides and tags.

[Polynucleotide Encoding Thermostable Cellobiohydrolase]

The polynucleotide according to the present invention encodes the thermostable cellobiohydrolase according to the present invention. By introducing an expression vector incorporating the polynucleotide into a host, the thermostable cellobiohydrolase described above can be produced by using the expression system of the host.

Specifically, the polynucleotide according to the present invention is a polynucleotide having any of the following nucleotide sequences (a1) to (e1), and a nucleotide sequence encoding a polypeptide having a cellobiohydrolase catalytic domain.

(a1) A nucleotide sequence encoding a polypeptide including the amino acid sequence represented by SEQ ID NO: 1, (b1) a nucleotide sequence encoding a polypeptide including an amino acid sequence in which at least one amino acid has been deleted, substituted, or added in the amino acid sequence represented by SEQ ID NO: 1, the polypeptide having a cellulose-binding function, (c1) a nucleotide sequence encoding a polypeptide including an amino acid sequence having 70% or greater sequence identity with the amino acid sequence represented by SEQ ID NO: 1, the polypeptide having a cellulose-binding function, (d1) a nucleotide sequence having 80% or greater sequence identity with a nucleotide sequence represented by SEQ ID NO: 2, and encoding a polypeptide having a cellulose-binding function, or (e1) a nucleotide sequence of a polynucleotide which hybridizes under stringent conditions with a polynucleotide including the nucleotide sequence represented by SEQ ID NO: 2, the nucleotide sequence encoding a polypeptide having a cellulose-binding function.

Examples of the polynucleotide according to the present invention include polynucleotides composed of nucleotide sequences of any of the following (a2) to (e2), and polypeptides composed of nucleotide sequences including the nucleotide sequences of any of the following (a2) to (e2).

(a2) A nucleotide sequence encoding a polypeptide including the amino acid sequence represented by SEQ ID NO: 3, (b2) a nucleotide sequence encoding a polypeptide including an amino acid sequence in which at least one amino acid has been deleted, substituted, or added in the amino acid sequence represented by SEQ ID NO: 3, the polypeptide having hydrolysis activity against a substrate of phosphoric acid swollen Avicel at least under conditions of 95° C. and pH 5.5, (c2) a nucleotide sequence encoding a polypeptide including an amino acid sequence having 70% or greater sequence identity with the amino acid sequence represented by SEQ ID NO: 3, the polypeptide having hydrolysis activity against a substrate of phosphoric acid swollen Avicel at least under conditions of 95° C. and pH 5.5, (d2) a nucleotide sequence having 80% or greater sequence identity with a nucleotide sequence represented by SEQ ID NO: 4, and encoding a polypeptide having hydrolysis activity against a substrate of phosphoric acid swollen Avicel at least under conditions of 95° C. and pH 5.5, or (e2) a nucleotide sequence of a polynucleotide which hybridizes under stringent conditions with a polynucleotide including the nucleotide sequence represented by SEQ ID NO: 4, the nucleotide sequence encoding a polypeptide having hydrolysis activity against a substrate of phosphoric acid swollen Avicel at least under conditions of 95° C.

In the present description, a "polynucleotide in which a nucleotide is deleted" means a polynucleotide in which a portion of the nucleotides that constitute the polynucleotide is missing (removed).

In the present description, a "polynucleotide in which a nucleotide is substituted" means a polynucleotide in which a nucleotide that constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing that is performed after the incubation is preferably a 1×SSC solution containing 0.1% by mass of SDS, and is more preferably a 0.1×SSC solution containing 0.1% by mass of SDS.

In the aforementioned nucleotide sequences of (a1) to (e1) and (a2) to (e2), it is preferable to select a degenerate codon having a high frequency of usage in the host. For example, the aforementioned nucleotide sequence of (a1) may be either the nucleotide sequence represented by SEQ ID NO: 2, or a nucleotide sequence obtained by modifying the nucleotide sequence represented by SEQ ID NO: 2 to codons having a higher frequency of usage in the host without changing the amino acid sequence encoded by the nucleotide sequence. This codon modification can be achieved using a known gene sequence variation technique or artificial gene synthesis.

The polynucleotide including the nucleotide sequence represented by SEQ ID NO: 2 or SEQ ID NO: 4 may be chemically synthesized based on the nucleotide sequence information, or may be obtained from the natural world using gene recombination techniques as either a full-length gene that encodes AR19G-166c4A-19-2 (hereafter sometimes referred to as the "AR19G-166c4A-19-2 gene" or the "gene clone AR19G-166c4A-19-2") or a partial region thereof including the cellobiohydrolase catalytic domain and the CBM. The full length of the AR19G-166c4A-19-2 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 2. The cDNA synthesized by a reverse transcription reaction using mRNA recovered from the sample as a template may also be used as a template.

In the aforementioned nucleotide sequences of (d1) and (d2), the sequence identity with the nucleotide sequence represented by SEQ ID NO: 2 or SEQ ID NO: 4 is not specifically limited as long as it is 80% or greater but less than 100%, but the sequence identity is preferably 85% or greater but less than 100%, more preferably 90% or greater but less than 100%, still more preferably 95% or greater but less than 100%, and most preferably 98% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity values between nucleotide sequences in the present invention were obtained by calculation on the basis of an alignment obtained from the publicly known homology search software BLASTN.

For example, each of the polynucleotides including an aforementioned nucleotide sequence of (b1), (b2), (c1), (c2), (d1) or (d2) can be artificially synthesized by deleting, substituting, or adding one or a plurality of nucleotides in a polynucleotide including the nucleotide sequence represented by SEQ ID NO: 2 or SEQ ID NO: 4. Further, the nucleotide sequence of (b1), (b2), (e1), (c2), (d1) or (d2) may also be a full-length sequence of a homologous gene of the AR19G-166c4A-19-2 gene or a partial sequence thereof. The homologous gene of the AR19G-166c4A-19-2 gene can be obtained by a gene recombination technique used in obtaining homologous genes of a gene for which the nucleotide sequence is already known.

The polynucleotide according to the present invention may have only the domains encoding the cellobiohydrolase catalytic domain and the CBM, or may also have, in addition to these domains, one or more other domains encoding a linker sequence, various types of signal peptides, or various types of tags or the like.

In other words, one aspect of the polynucleotide according to the present invention contains a nucleotide sequence of one of the aforementioned (a2) to (e2), and also contains, according to need, a domain encoding at least one moiety selected from the group consisting of signal peptides and tags.

[Expression Vector]

The expression vector according to the present invention incorporates the aforementioned polynucleotide according to the present invention, and is capable of expressing, in a host cell, a polypeptide having cellobiohydrolase activity at least under conditions of 95° C. and pH 5.5. In other words, the expression vector of the present invention is an expression vector into which the polynucleotide according to the present invention has been incorporated in a state capable of expressing the thermostable cellobiohydrolase according to the present invention. More specifically, an expression cassette composed of, in order from the upstream side, DNA having a promoter sequence, the aforementioned polynucleotide according to the present invention and DNA having a terminator sequence, must be incorporated into the expression vector. Incorporation of the polynucleotide into the expression vector can be achieved using known gene recombination techniques, or a commercially available expression vector preparation kit may be used.

The aforementioned expression vector may be an expression vector for introduction into a prokaryotic cell such as *E. coli*, or an expression vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of cells transformed by the expression vector and non-transformed cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the thermostable cellobiohydrolase according to the present invention can be expressed. Conventionally known cellobiohydrolases tend to have a narrow range of expression hosts, meaning heterologous expression is often difficult. However, the thermostable cellobiohydrolase according to the present invention can be expressed in a wide range of expression hosts, including *E. coli*, yeasts, filamentous fungi and higher plant chloroplasts. Accordingly, the host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced. By culturing a transformant of *E. coli*, the thermostable cellobiohydrolase according to the present invention can be generated more easily and in large amounts.

On the other hand, because proteins are glycosylated in eukaryotic cells, by using a transformant of a eukaryotic cell, a thermostable cellobiohydrolase can be generated which exhibits superior thermal stability to that achieved by using a transformant of a prokaryotic cell.

There are no particular limitations on the method used for producing the transformant using the expression vector, and the types of methods typically used in the production of transformants can be employed. Examples of methods that can be used include an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable Cellobiohydrolase]

The method for producing a thermostable cellobiohydrolase according to the present invention is a method for generating a thermostable cellobiohydrolase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable cellobiohydrolase according to the present invention can be expressed constitutively within the transformant. On the other hand, in the case of a transformant produced using a so-called expression inducible promoter to induce the expression by means of a specific compound or temperature condition or the like, the thermostable cellobiohydrolase according to the present invention can be expressed in the transformant by conducting an induction treatment suitable for the respective expression-inducing condition.

The thermostable cellobiohydrolase generated by the transformant may be used in a state where it is retained inside the transformant, or may be extracted from the transformant and purified.

The method used for extracting and purifying the thermostable cellobiohydrolase from the transformant is not particularly limited, as long as the method does not impair the activity of the thermostable cellobiohydrolase, and extraction can be carried out by methods commonly used for extracting polypeptides from cells or biological tissue. Examples of the method include a method in which the transformant is immersed in an appropriate extraction buffer to extract the thermostable cellobiohydrolase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable cellobiohydrolase in the liquid extract can be purified by known purification methods such as a salting-out method, ultrafiltration method, or chromatography method.

If the thermostable cellobiohydrolase according to the present invention is expressed in the transformant in a state having a secretory signal peptide, then a solution containing the thermostable cellobiohydrolase can be readily obtained by culturing the transformant and then collecting the culture liquid supernatant obtained by removal of the transformant from the obtained culture. Further, if the thermostable cellobiohydrolase according to the present invention has a tag such as an His tag, then the thermostable cellobiohydrolase in the liquid extract or in the culture supernatant can be easily purified by an affinity chromatography method using the tag.

In other words, the method for producing a thermostable cellobiohydrolase according to the present invention includes generating the thermostable cellobiohydrolase within the transformant according to the present invention, and also includes, according to need, extracting the thermostable cellobiohydrolase from the transformant and purifying the thermostable cellobiohydrolase.

[Glycoside Hydrolase Mixture]

The glycoside hydrolase mixture according to the present invention includes the aforementioned thermostable cellobiohydrolase according to the present invention or a thermostable cellobiohydrolase produced by the method for producing a thermostable cellobiohydrolase according to the present invention, and at least one other glycoside hydrolase. The thermostable cellobiohydrolase produced by the aforementioned method for producing a thermostable cellobiohydrolase according to the present invention may be in a state where it is incorporated inside the transformant, or may be extracted from the transformant and purified. By using the thermostable cellobiohydrolase according to the present invention as a mixture with one or more other glycoside hydrolases in a cellulose hydrolysis reaction, materials composed of lignocellulose containing persistent cellulose can be degraded more efficiently.

There are no particular limitations on the other glycoside hydrolase besides the aforementioned thermostable cellobiohydrolase included in the glycoside hydrolase mixture, as long as it exhibits cellulose hydrolysis activity. Examples of the other glycoside hydrolase besides the aforementioned cellobiohydrolase included in the glycoside hydrolase mixture include hemicellulases such as xylanases and β-xylosidases, cellobiohydrolases other than the thermostable cellobiohydrolase of the present invention, β-glucosidases and endoglucanases. The glycoside hydrolase mixture according to the present invention is preferably a mixture containing at least one glycoside hydrolase selected from among hemicellulases and endoglucanases in addition to the aforementioned thermostable cellobiohydrolase according to the present invention, and is more preferably a mixture containing both a hemicellulase and an endoglucanase in addition to the aforementioned thermostable cellobiohydrolase. Among the various possibilities, the glycoside hydrolase mixture is preferably a mixture containing at least one glycoside hydrolase selected from the group consisting of xylanases, β-xylosidases, cellobiohydrolases other than the thermostable cellobiohydrolase according to the present invention and endoglucanases in addition to the aforementioned thermostable cellobiohydrolase of the present invention, and is more preferably a mixture containing all of a xylanase, a β-xylosidase, a cellobiohydrolase other than the thermostable cellobiohydrolase according to the present invention and an endoglucanase in addition to the aforementioned thermostable cellobiohydrolase.

The other glycoside hydrolase included in the glycoside hydrolase mixture is preferably a thermostable glycoside hydrolase having glycoside hydrolase activity at least at 70° C., is more preferably a thermostable glycoside hydrolase having glycoside hydrolase activity at 70 to 95° C., and is still more preferably a thermostable glycoside hydrolase having glycoside hydrolase activity at 70 to 105° C. By ensuring that all of the enzymes contained in the glycoside hydrolase mixture are thermostable (for example, have an optimum temperature for the enzymatic activity or a thermal denaturation temperature for the enzyme protein of 70° C. or higher), the cellulose hydrolysis reaction by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material containing cellulose, such as a material composed of lignocellulose containing cellulose, it becomes possible to conduct a hydrolysis reaction of the material in a high-temperature environment in which the hydrolysis temperature is from 70 to 95° C. (namely, a high-temperature hydrolysis). With this high-temperature hydrolysis, the amount of enzymes used and the time required for the hydrolysis can be reduced markedly, and the hydrolysis costs can be cut dramatically.

[Method for Producing Cellulose Degradation Product]

The method for producing a cellulose degradation product according to the present invention is a method for obtaining a cellulose degradation product by hydrolyzing a material containing cellulose with the thermostable cellobiohydrolase according to the present invention. More specifically, the cellulose degradation product (for example, a degradation product containing cellobiose and glucose and the like) is produced by bringing the material containing cellulose into contact with the thermostable cellobiohydrolase according to the present invention, the transformant according to the present invention, a thermostable cellobiohydrolase produced using the method for producing a thermostable cellobiohydrolase according to the present invention, or the glycoside hydrolase mixture according to the present invention.

There are no particular limitations on the material containing cellulose, provided the material contains cellulose. Specific examples of the material include cellulosic biomass such as weeds and agricultural waste materials, or used paper or the like. The material containing cellulose is preferably subjected to a physical treatment such as crushing or shredding, a chemical treatment with acid or alkali or the like, or a treatment such as immersion or dissolution in an appropriate buffer, prior to being brought into contact with the thermostable cellobiohydrolase according to the present invention.

The reaction conditions for the cellulose hydrolysis reaction by the thermostable cellobiohydrolase according to the present invention may be any conditions under which the thermostable cellobiohydrolase exhibits cellobiohydrolase activity. For example, in the absence of divalent metal ions, the reaction is preferably conducted at a temperature of 60 to 100° C. and a pH of 4.5 to 6.5, and is more preferably conducted at a temperature of 50 to 100° C. and a pH of 4.5 to 6.5. Further, in the presence of divalent metal ions, the reaction is preferably conducted at a temperature of 80 to 105° C. and a pH of 4.5 to 6.5, and is more preferably conducted at a temperature of 70 to 105° C. and a pH of 4.5 to 6.5. The reaction time for the hydrolysis reaction may be adjusted appropriately with due consideration of the type of cellulose material supplied to the hydrolysis reaction, and the method of pretreatment and the amount and the like of the cellulose material. For example, the hydrolysis reaction may be performed for a reaction time of 10 minutes to 100 hours, but in the case of degradation of cellulosic biomass, the hydrolysis reaction is typically performed for a reaction time of 1 to 100 hours.

In the hydrolysis reaction of the material containing cellulose, it is also preferable to use at least one other type of glycoside hydrolase in addition to the thermostable cellobiohydrolase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 70° C., and preferably at least at temperatures of 70 to 100° C. Further, one aspect of the aforementioned method for producing a cellulose degradation product uses the thermostable cellobiohydrolase according to the present invention, the transformant according to the present invention, or a thermostable cellobiohydrolase produced by the method for producing a thermostable cellobiohydrolase according to the present invention, whereas another aspect of the method uses the aforementioned glycoside hydrolase mixture.

EXAMPLES

Next, the present invention is described in further detail based on a series of examples, but the present invention is in no way limited by the following examples.

[Example 1] Cloning of Novel Thermostable Cellobiohydrolase from Hot Spring Soil <1> DNA Extraction from Hot Spring Soil and Whole Genome Sequencing (WGS)

With the purpose of searching for genes of thermostable cellobiohydrolases (having an optimum temperature of 55° C. or higher) and ultra-thermostable cellobiohydrolases (having an optimum temperature of 80° C. or higher), soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, mud and biomat from five sampling points (metagenomic DNA samples N2, AR19, AR15, OJ1 and H1) at three locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples using a DNA extraction kit (ISOIL Large for Beads ver. 2, manufactured by Nippon Gene Co., Ltd.). Five µg of the extracted DNA was subjected to shotgun sequencing of the metagenomic DNA using a sequencer GS FLX Titanium 454 manufactured by Roche Diagnostics Ltd.

Metagenomic DNA sequencing of the hot spring soil sample AR15 yielded a whole genome sequence (WGS) data set having an average read length of 396 bp, a total read number of 2,766,332, and a total quantity of sequenced genomes of 1,106,243,280 bp.

<2> Assembly and Statistics of Hot Spring Metagenomic Data

The output from the Roche 454 (sff file) was subjected to low-quality read trimming and de novo assembly using Genomics Workbench Ver. 4 software (manufactured by CLC bio, Inc.).

The total contig length of all contigs assembled to at least 500 bp totaled 159,587,150 bp, and this data set was used for cellulase gene analysis. The total read number following trimming was 2,766,328 reads, and these reads were assembled into contigs having an average of 1,230 bp (a total of 129,742 contigs), of which the maximum contig length was 105,977 bp.

<3> Prediction of open reading frames (ORFs) of cellobiohydrolase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: 2011/12/9) from the UniProt database (http://www.uniprot.org/), and a proteome local database of these glycoside hydrolase genes was constructed. The annotation software MetaGeneAnnotator (Noguchi et al., MetaGeneAnnotator: Detecting Species-Specific Patterns of Ribosomal Binding Site for Precise Gene Prediction in Anonymous Prokaryotic and Phage Genomes, DNA Res., 2008, 15, pp. 387 to 396) was used to predict gene regions (=open reading frames) from the contig sequences obtained above in section <2>. In order to extract glycoside hydrolase genes from the predicted ORFs, reference was made to the aforementioned local database using BLASTP (blastall ver. 2.2.18). Furthermore, the option conditions for BLASTP were set such that: "Filter query sequence=false", "Expectation value (E)<1e$^{-20}$" (hereafter, default values were set such that: "Cost to open a gap=-1" "Cost to extended gap=-1", "X dropoff value for gapped alignment=0", "Threshold for extending hits=0", and "Word size=default"), and the hit sequences were collected as glycoside hydrolase genes.

<4> Glycoside Hydrolase (GH) Family Classification of Genes

Functional classification of the sequences collected above in section <3>, including various sequences containing glycoside hydrolases such as cellulases, endohemicellulases and debranching enzymes, was performed with reference to the protein functional domain sequence database Pfam HMMs (Pfam version 23.0 and HMMER v2.3; Finn et al., Nucleic Acids Research Database, 2010, Issue 38, pp. D211 to 222). Specifically, the glycoside hydrolase (GH) family of each sequence was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff <1e$^{-5}$; Database=Pfam_fs (models that can be used to find fragments of the represented domains in a sequence)).

Based on homology search results by BLASTP and reference to Pfam HMMs using the sequence data from the hot spring soil sample AR19, 61 ORFs were predicted as being cellobiohydrolase genes. One of these was an ORF in which a novel sequence of the CBM family 2 had been added to the N-terminal side of the sequence of a one-amino acid mutant (R299Q) AR19G-166-QA of the known AR19G-166RA. Primers were designed for this ORF, and the gene was cloned by PCR using the hot spring soil DNA that had been amplified using a genome DNA amplification kit (GenomiPhi V2 DNA Amplification Kit, manufactured by GE Healthcare, Inc.) as a template. As a result, a cellobiohydrolase gene AR19G-166c4A-19-2 was isolated from the open reading frame AR19G-166c4A having a cellobiohydrolase sequence of GH family 6 with the CBM family 2 at the 5'-terminal.

<5> Open Reading Frame AR19G-166c4A

The open reading frame AR19G-166c4A encoded a polypeptide (SEQ ID NO: 3) composed of 590 amino acid residues, and was a partial length sequence (SEQ ID NO: 4) in which the aforementioned polypeptide started from an alanine (A) as the amino acid residue at position 1, and the 3'-end ended with a termination codon. Based on the sequence homology of the motif, it was predicted that in the amino acid sequence encoded by the open reading frame AR19G-166c4A, the 102 amino acid residues from the cysteine (C) at position 2 through to the cysteine (C) at position 103 represented the CBM family 2 domain, and the 427 amino acid residues from the leucine (L) at position 164 through to the proline (P) at position 590 represented the catalytic domain of the glycoside hydrolase family 6. This CBM family 2 domain was a novel sequence that exhibited 64% amino acid sequence identity in the CBM domain with the CBM2 domain (the domain composed of the amino acids from positions 29 to 128 of SEQ ID NO: 9) of the α-L-arabinofuranosidase of an *Actinomyces Microbispora* subspecies. The sequence homology was calculated using the ClustalW algorithm.

FIG. 1 shows the alignment of the amino acid sequence (SEQ ID NO: 3) of the polypeptide presumed to be encoded by the open reading frame AR19G-166c4A and the amino acid sequence of the CBM2 domain of the α-L-arabinofuranosidase of the *Actinomyces Microbispora* subspecies (SEQ ID NO: 9). In FIG. 1, the amino acids shown in white on black are the amino acid residues identical to both amino acid sequences, and "-" indicates a gap in a sequence.

<6> Cellobiohydrolase Gene AR19G-166c4A-19-2

PCR cloning was used to isolate the cellobiohydrolase gene AR19G-166c4A-19-2 from the open reading frame AR19G-166c4A. The AR19G-166c4A-19-2 gene included a nucleotide sequence composed of 1,773 bp that was identical with the open reading frame AR19G-166c4A.

<7> Expression and Purification of Cellobiohydrolase Protein

Using a forward primer including a nucleotide sequence represented by SEQ ID NO: 7 (5'-GTGATGGCCTGCCA-GGTGTCCTAC-3': wherein six nucleotides (GTGATG) were added to the 5'-end of the nucleotide sequence represented by SEQ ID NO: 5, and the 5'-end was phosphorylated), and a reverse primer including a nucleotide sequence of SEQ ID NO: 8 (5'-ATGCAGAGCTCTTAGGGTTG-GATCGGCGGATAG-3': wherein a recognition sequence for the restriction enzyme SacI was added to the 5'-end of the nucleotide sequence represented by SEQ ID NO: 6, the SacI being a sequence used for vector insertion), a PCR product that had been amplified by KOD-Plus-Neo (manufactured by Toyobo Co., Ltd.) was inserted into a pLEAD5 vector (manufactured by Nippon Gene Co., Ltd.), and transformed into an *E. coli* JM109 strain. The nucleotide sequence represented by SEQ ID NO: 5 is homologous (identical) with the partial sequence composed of the nucleotides from positions 1 to 18 of the nucleotide sequence represented by SEQ ID NO: 4. Further, the nucleotide sequence represented by SEQ ID NO: 6 is complementary with the partial sequence composed of the nucleotides from positions 1,752 to 1,773 of the nucleotide sequence represented by SEQ ID NO: 4. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation). The gene clone AR19G-166c4A-19-2 was obtained from the open reading frame AR19G-166c4A by PCR cloning.

The transformed E. coli clone having the AR19G-166c4A-19-2/pLEAD5 plasmid for which the sequence had been confirmed was inoculated into a Turbo Broth medium (manufactured by Athena Environmental Sciences, Inc.) containing 50 mg/L of ampicillin, and was cultured for about 20 hours to express the target protein. Following culturing, the E. coli was collected by centrifugation, and an amount of 50 mM Tris-HCl buffer (pH 8.0) equivalent to 1/10 of the volume of the culture liquid was added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant E. coli containing the target protein. This gene recombinant E. coli crude extract was filtered through a filter (pore size φ=0.45 µm, manufactured by EMD Millipore Corporation), and the resulting filtrate was used as a gene recombinant E. coli homogeneous supernatant.

The gene recombinant E. coli homogeneous supernatant was loaded onto an ion exchange column HiTrap Q HP (manufactured by GE Healthcare, Inc.) equilibrated with a 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in a 50 mM Tris-HCl buffer (pH 8.0) containing 1 M of NaCl. The fractions exhibiting cellobiohydrolase activity were pooled, and a centrifugal ultrafiltration membrane VIVAS-PIN 20 (manufactured by Sartorius stedim Biotech SA) was used to exchange the buffer to a 50 mM Tris-HCl buffer (pH 8.0) containing 750 mM of ammonium sulfate. The fractions with cellobiohydrolase activity following the buffer exchange were loaded onto a hydrophobic interaction separation column HiTrap Phenyl HP (manufactured by GE Healthcare, Inc.) equilibrated with the same buffer solution, and the proteins were fractionated with a concentration gradient of 0 to 100% in a 50 mM Tris-HCl buffer (pH 8.0). The fractions exhibiting cellobiohydrolase activity were pooled and then concentrated by using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with a 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting cellobiohydrolase activity were pooled, and a buffer exchange to a 50 mM Tris-HCl buffer (pH 8.0) and subsequent concentration were performed, yielding a purified enzyme with a final concentration of about 1 mg/mL.

The gene recombinant E. coli homogenous supernatant and the purified enzyme (purified cellobiohydrolase protein) were checked by SDS-PAGE analysis (SDS-polyacrylamide gel electrophoresis). The SDS electrophoresis of the gene recombinant E. coli homogenous supernatant and the purified enzyme was performed using a Mini-PROTEAN TGX Stain-Free gel (manufactured by Bio-Rad Laboratories, Inc.). The supernatant and the purified enzyme were each mixed with Tris-SDS βME treatment solution (manufactured by Cosmo Bio Co. Ltd.) at 1:1, and following treatment of the thus obtained electrophoresis samples at 100° C. for 10 minutes, a 10 µL sample of the gene recombinant E. coli homogenous supernatant and a 1 µg sample of the purified enzyme respectively were subjected to electrophoresis. Following completion of the electrophoresis, the protein bands were visualized and detected by CBB staining and Western blotting.

In the case of the Western blotting, following the SDS electrophoresis, the proteins were transferred onto a polyvinylidene fluoride membrane using a transfer apparatus Trans-Blot SD (manufactured by Bio-Rad Laboratories, Inc.) and a Trans-Blot Turbo Transfer Pack (manufactured by Bio-Rad Laboratories, Inc.). The proteins on the membrane were reacted with 1000-fold diluted rabbit primary antibodies. The rabbit primary antibodies were produced by synthesizing a polypeptide including the 20 amino acid residues from positions 384 to 403 (CDPNGQSRYNSAY-PTGALPN) encoded by AR19G-166-RA, and carrying out an affinity purification of the serum from an immunized rabbit (manufactured by Operon Biotechnologies, Inc.). Detection of the primary antibody bound to the protein was conducted using a Fast Western Blotting kit (manufactured by Pierce Biotechnology, Inc.), and the detection of chemiluminescent signals was conducted using an imaging apparatus Ez-Capture MG (manufactured by ATTO Corporation).

FIG. 2 shows the results of CBB staining (FIG. 2(A)) and the results of Western blotting (FIG. 2(B)) of the SDS-PAGE analyses of the gene recombinant E. coli homogenous supernatant prepared from the transformed E. coli into which the AR19G-166c4A-19-2 gene had been introduced, and the purified enzyme produced from the gene recombinant E. coli homogenous supernatant. The figure shows electrophoretic patterns in which lane 1 represents a protein mass marker, lane 2 represents the gene recombinant E. coli homogenous supernatant, and lane P represents the purified enzyme. The results revealed that in both the CBB staining and the Western blotting, a strong band was observed in the gene recombinant E. coli homogenous supernatant (lane 2) near the mass of 63.4 kDa expected from the amino acid sequence (SEQ ID NO: 3), and a single band corresponding with this band (indicated by an arrow in the figure) was observed in the purified enzyme (lane 3).

<8> Cellobiohydrolase Activity

The cellobiohydrolase activity of the enzyme protein (AR19G-166c4A-19-2) encoded by the AR19G-166c4A-19-2 gene against substrates of PSA and Avicel was investigated. In the measurements, a solution prepared by diluting the purified enzyme obtained above in section <7> with a 0.05 M Tris-HCl buffer (pH 8.0) to obtain a concentration of 1 mg/mL was used.

The PSA used as the substrate was prepared by first dissolving an Avicel powder (microcrystalline cellulose powder, manufactured by Merck & Co., Inc.) in a phosphoric acid solution, subsequently adding purified water to cause precipitation, and then washing until a pH of 5 or greater was obtained. The PSA used in the experiments described below was all prepared by the above method.

A ThermoMixer (manufactured by Eppendorf AG) was used for the reaction, a sample tube with a volume of 1.5 mL was used as the reaction vessel, and the reaction solution was composed of 10 µL of the diluted purified enzyme, 40 µL of purified water, 50 µL of a 200 mM acetate buffer (pH 5.5), and 100 µL of a 1% by mass substrate solution. In the case of a PSA substrate, reaction was performed at 95 to 110° C. using a Reacti-Therm (manufactured by GL Sciences Inc.), a glass vial with a volume of 1.5 mL was used as the reaction vessel, and the reaction solution volume was 400 µL. The reaction solution was composed of 20 µL of the diluted purified enzyme, 80 µL of purified water, 100 µL of a 200 mM acetate buffer (pH 5.5), and 200 µL of a 1% by mass PSA solution.

In all the measurements, a mixed solution prepared by replacing the purified enzyme solution with a 50 mM Tris-HCl buffer (pH 8.0) and then reacting the solution under the same conditions was used as a control. Further, the substrate solution and the mixed solution containing the purified enzyme solution, the purified water and the buffer were held separately at the reaction temperature for five minutes (pre-incubation) before being mixed to initiate the reaction. Following completion of a 20-minute reaction in the case of PSA or a 60-minute reaction in the case of Avicel, 3,5-dinitrosalicylic acid reagent (DNS solution) was added to each reaction solution in a volume equal to that of the solution, and the resulting mixture was heated at 100° C. for 5 minutes, cooled on ice for 5 minutes, and then centrifuged at 17,500 g for 5 minutes at room temperature to obtain a supernatant. The amount of reducing sugars within the supernatant was determined by measuring the absorbance at 540 nm using a spectrophotometer, calculating the amount of reducing sugars using a calibration curve prepared with glucose, and then calculating the amount of reducing sugars produced by the enzymatic hydrolysis based on the difference from the control. The enzymatic activity for producing 1 mmol of reducing sugars per minute was defined as 1 U, and the value obtained by dividing this activity by the amount of protein was defined as the specific activity (U/mg). Each measurement was performed for three independent experiments, and a mean value and a standard error were determined.

<9> Temperature Dependency of AR19G-166c4A-19-2

The temperature dependency of the PSA hydrolysis activity and the Avicel hydrolysis activity of AR19G-166c4A-19-2 was investigated.

Specifically, in measurements of the temperature dependency of the PSA hydrolysis activity, with the exception of setting the reaction temperature to 50, 60, 65, 70, 75, 80, 85, 90, 95, 100, 105 or 110° C., reaction was performed in the same manner as that described above in section <8>, and for each temperature, the amount of reducing sugars produced by the enzymatic hydrolysis was determined and the PSA hydrolysis activity (U/mg) was calculated.

In measurements of the temperature dependency of the Avicel hydrolysis activity, with the exception of setting the reaction temperature to 50, 60, 70, 75, 80, 85, 90 or 99° C., reaction was performed in the same manner as that described above in section <8>, and for each temperature, the amount of reducing sugars produced by the enzymatic hydrolysis was determined and the Avicel hydrolysis activity (U/mg) was calculated.

Further, measurements were also performed using reaction solutions in which a 10 mM aqueous solution of $CaCl_2$ was added instead of the purified water, and for each temperature, the amount of reducing sugars produced by the enzymatic hydrolysis was determined and the PSA hydrolysis activity (U/mg) and the Avicel hydrolysis activity (U/mg) were calculated.

Moreover, as a comparison, similar measurements were performed for AR19G-166-QA which lacks a CBM domain.

Figure 3:
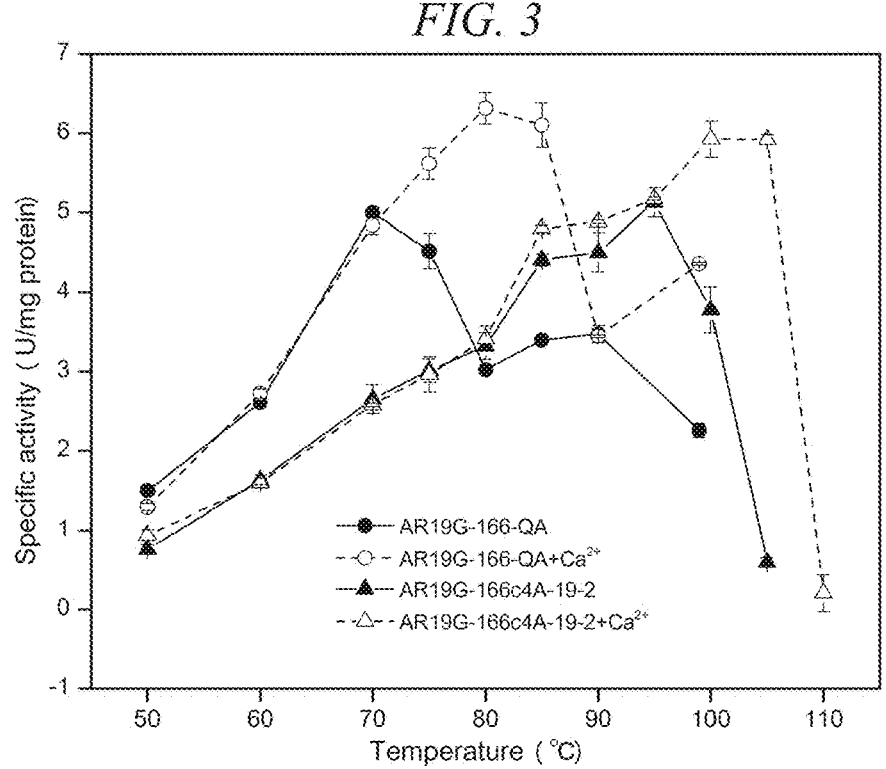
FIG. 3 is a diagram showing the results of measuring the PSA hydrolysis activity (pH 5.5) at various temperatures, either in the presence of calcium ions or in the absence of calcium ions, of the AR19G-166c4A-19-2 protein obtained by expressing the AR19G-166c4A-19-2 gene in *E. coli* and the AR19G-166-QA protein obtained by expressing the AR19G-166-QA gene in *E. coli* in Example 1.

The measurement results for the PSA hydrolysis activity are shown in FIG. 3. AR19G-166c4A-19-2 exhibited PSA hydrolysis activity across a temperature range from 50 to 105° C. (FIG. 3). In particular, in the presence of calcium ions, AR19G-166c4A-19-2 exhibited high PSA hydrolysis activity even at 100 to 105° C.

The optimum temperature ($T_{opt}$) at which the highest activity was observed was 95° C. in the absence of calcium ions (labeled "AR19G-166c4A-19-2" in the figure) and 105° C. in the presence of calcium ions (labeled "AR19G-166c4A-19-2+$Ca^{2+}$" in the figure). In contrast, the optimum temperature for AR19G-166-QA was 70° C. in the absence of calcium ions (labeled "AR19G-166-QA" in the figure) and 80° C. in the presence of calcium ions (labeled "AR19G-166-QA+$Ca^{2+}$" in the figure). These results indicate that the presence of the CBM increased the optimum temperature of the PSA hydrolysis activity by as much as 25° C.

Figure 4:
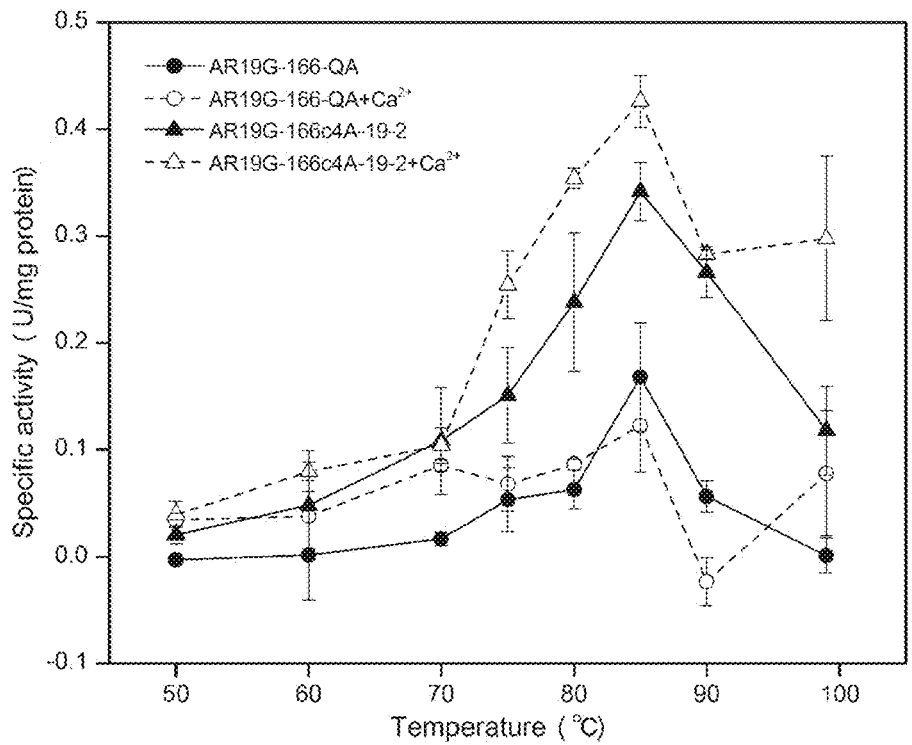
FIG. 4 is a diagram showing the results of measuring the Avicel hydrolysis activity (pH 5.5) at various temperatures, either in the presence of calcium ions or in the absence of calcium ions, of the AR19G-166c4A-19-2 protein obtained by expressing the AR19G-166c4A-19-2 gene in *E. coli* and the AR19G-166-QA protein obtained by expressing the AR19G-166-QA gene in *E. coli* in Example 1.

The measurement results for the Avicel hydrolysis activity are shown in FIG. 4. The optimum temperature for both AR19G-166c4A-19-2 and AR19G-166-QA was 85° C., regardless of the presence or absence of calcium ions. However, in the case of AR19G-166c4A-19-2, a dramatic increase in the Avicel hydrolysis activity was observed. The average values for the Avicel hydrolysis activity of AR19G-166-QA at the optimum temperature of 85° C., in the absence or presence of calcium ions, were 0.17±0.05 U/mg and 0.12±0.04 U/mg respectively, whereas the corresponding values for AR19G-166c4A-19-2 were 0.34±0.03 U/mg and 0.43±0.02 U/mg respectively. These results indicate that the presence of the CBM increased the Avicel hydrolysis activity by 2-fold in the absence of calcium ions, and by 3.6-fold in the presence of calcium ions.

<10> Thermal Stability Measurement of Cellobiohydrolase by Differential Scanning Fluorimetry Differential scanning fluorimetry (DSF) is one of the methods of measuring the thermal denaturation of proteins using a fluorescent dye and a real-time PCR machine, and can be applied to all manner of proteins. The fluorescent dyes used in DSF such as SYPRO Orange emit fluorescence under nonpolar conditions when bound to a hydrophobic region, while the emission is suppressed under the polar conditions produced upon dissolution in water. Usually, the protein structure unfolds at the thermal denaturation temperature, and the internal hydrophobic regions of the protein are exposed at the protein surface. When SYPRO Orange binds to such an exposed hydrophobic region, excitation light having a wavelength of 470 to 480 nm causes emission of a strong fluorescence having a peak near a wavelength of 595 nm. By increasing the temperature of the protein solution at regular intervals in a stepwise manner and measuring the fluorescence intensity, the thermal denaturation temperature (=change point of the fluorescence intensity) can be calculated.

Measurements were performed using a purified enzyme solution prepared by dissolving the purified enzyme AR19G-166c4A-19-2 obtained above in section <7> in water at a concentration of 1 mg/mL, or a purified enzyme solution prepared by dissolving AR19G-166-QA in water at a concentration of 1 mg/mL.

Specifically, 2 μL of 100-fold diluted SYPRO Orange (manufactured by Life Technologies Inc.), 1 μL of the purified enzyme solution with a concentration of 1 mg/mL, 5 μL of a 200 mM acetate buffer (pH 5.5) and 12 μL of either purified water or a solution prepared by mixing purified water and a 10 mM $CaCl_2$ solution in a ratio of 2:1 were added to each well of a 96-well PCR plate (Multiplate 96 Well PCR Plate MLL-9651, manufactured by Bio-Rad Laboratories, Inc.) so that the volume in each well was 20 μL. The PCR plate was sealed with Optical Flat 8-Cap Strips (manufactured by Bio-Rad Laboratories, Inc.), the temperature of each well was increased in steps of 0.2° C. from 30° C. up to 100° C. using a real-time PCR machine (CFX96 Touch Real-Time PCR System, manufactured by Bio-Rad Laboratories, Inc.), and following a pause of 10 seconds after each target temperature was achieved, the fluorescence intensity of each well was measured simultaneously. The SYPRO Orange was excited by a light emitting diode (LED) having a wavelength range of 450 to 490 nm, the emitted light from the SYPRO Orange was passed through a band pass filter having a range of 560 to 580 nm, a CCD camera was used to measure the fluorescence intensity, and the change in fluorescence intensity was plotted as a function of temperature. The thermal denaturation temperature (melting temperature; Tm value) was defined as the local minimum value of the first derivative of the fluorescence intensity curve plotted as a function of temperature ("−d(Fluorescence)/dt" shown on the Y axis of FIG. 5(B)). Data analysis was conducted using the analysis software CFX Manager (manufactured by Bio-Rad Laboratories, Inc.) supplied with the real-time PCR machine. Each measurement was performed for three independent experiments, and a mean value and a standard error were determined.

Figure 5:
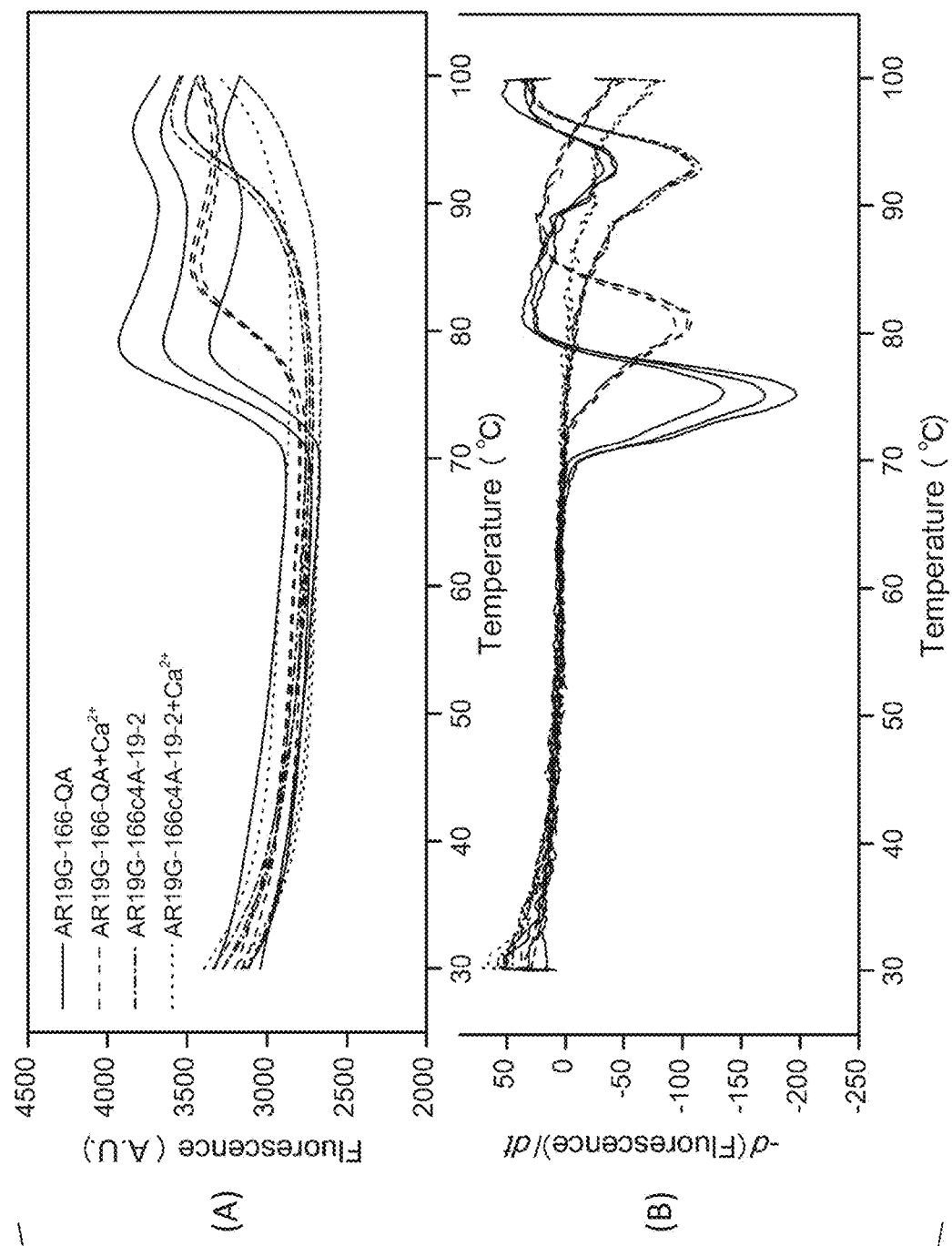
FIG. 5 consists of a diagram (A) and a diagram (B).

FIG. 5 shows the change in the fluorescence intensity of SYPRO Orange measured by the DSF method and caused in association with the thermal denaturation exhibited by the enzyme proteins of AR19G-166c4A-19-2 and AR19G-166-QA. FIG. 5(A) shows the actual measurement data, whereas FIG. 5(B) shows the first derivatives "−d(Fluorescence)/dt" of the fluorescence intensity change curves of FIG. 5(A).

The first derivative of the fluorescence intensity of AR19G-166c4A-19-2 (no $CaCl_2$ addition) had a local minimum point at 93.0±0° C., indicating that thermal denaturation occurs at that temperature. This temperature was similar to the optimum temperature of 95° C. for the enzyme determined from the PSA hydrolysis activity. Further, under the conditions including added $CaCl_2$, the fact that a local minimum point had not appeared even when 100° C. had been reached suggested a thermal denaturation temperature exceeding 100° C. On the other hand, the corresponding average values for the thermal denaturation temperature for AR19G-166-QA were 75.3±0.1° C. (no $CaCl_2$ addition) and 80.9±0.2° C. ($CaCl_2$ addition), which were similar values to the optimum temperatures of 70° C. (no $CaCl_2$ addition) and 80° C. ($CaCl_2$ addition) for the enzyme determined from the PSA hydrolysis activity.

<11> Effect of CBM Domain on Cellobiohydrolase Activity

In order to confirm the effect obtained when the CBM domain of AR19G-166c4A-19-2 was added to other enzymes, a cellobiohydrolase AR19G-166c4A-19-2-1 (SEQ ID NO: 11) having the CBM domain described above added to AR19G-166-RA was prepared and subjected to measurements of the Avicel hydrolysis activity. The AR19G-166c4A-19-2-1 gene (SEQ ID NO: 12) was prepared by using a QuikChange Site-Directed Mutagenesis Kit (manufactured by Agilent Technologies, Inc.) to substitute the glutamine at position 462 of AR19G-166c4A-19-2 with an arginine. Specifically, the preparation was conducted using AR19G-166c4A-19-2/pLEAD5 as a template, and using a mutagenesis primer 1 composed of the nucleotide sequence represented by SEQ ID NO: 13 and a mutagenesis primer 2 composed of the nucleotide sequence represented by SEQ ID NO: 14. Expression and purification of the AR19G-166c4A-19-2-1 was performed in a similar manner to that described above in section <7>, and the temperature dependency of the cellobiohydrolase activity was investigated in a similar manner to that described above in section <9>. As a comparison, the same measurements were performed for AR19G-166-RA having no CBM.

Figure 6:
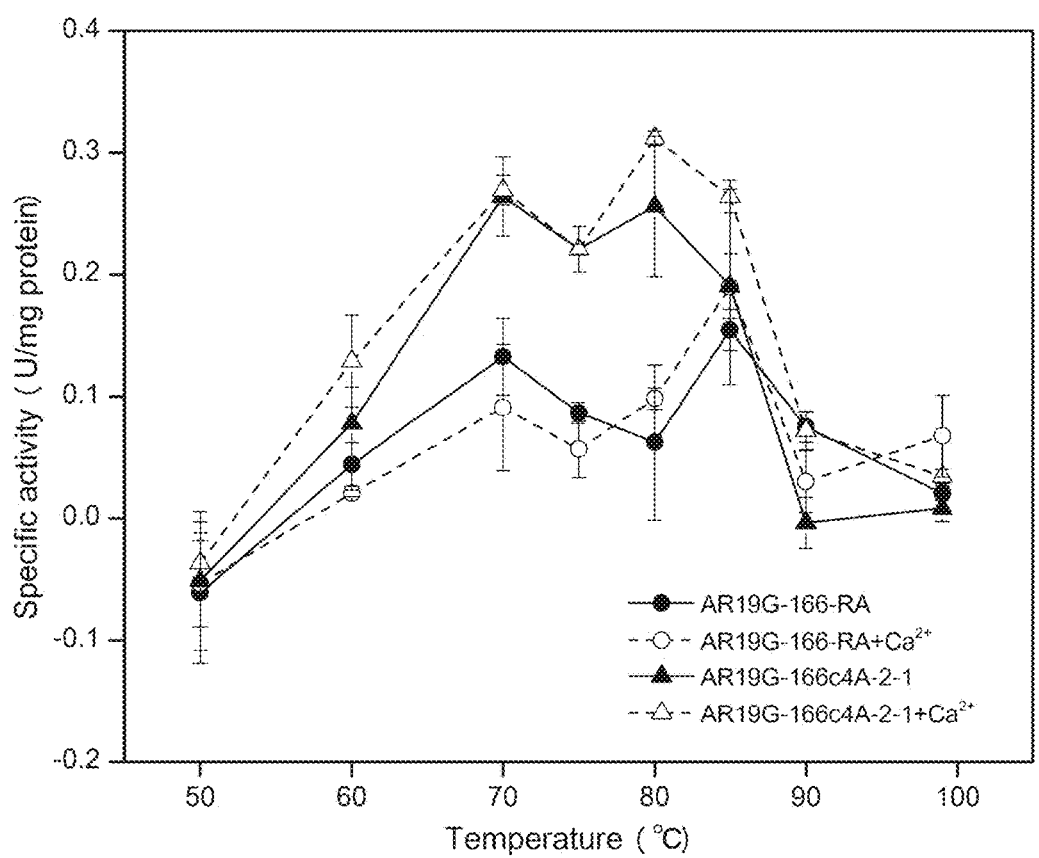
FIG. 6 is a diagram showing the results of measuring the Avicel hydrolysis activity (pH 5.5) at various temperatures, either in the presence of calcium ions or in the absence of calcium ions, of the AR19G-166-RA protein, and the AR19G-166c4A-19-2-1 protein obtained by adding the CBM of the AR19G-166c4A-19-2 protein to the AR19G-166-RA protein.

The measurement results for the Avicel hydrolysis activity are shown in FIG. 6. The AR19G-166c4A-19-2-1 exhibited a dramatic increase in the Avicel hydrolysis activity in the temperature range from 60 to 85° C. compared with the AR19G-166-RA having no CBM. The average values for the Avicel hydrolysis activity of AR19G-166c4A-19-2-1 at 80° C. were 0.26±0.06 U/mg in the absence of calcium ions and 0.31±0.01 U/mg in the presence of calcium ions, whereas the corresponding values for AR19G-166-RA were 0.06±0.06 U/mg and 0.10±0.01 U/mg respectively. These results indicate that the presence of the CBM increased the Avicel hydrolysis activity by 4.3-fold (or by 3.1-fold in the presence of calcium ions).

As these results indicate, by adding the CBM of the thermostable cellobiohydrolase according to the present invention to other cellobiohydrolase enzymes, the cellobiohydrolase activity of those other enzymes can be increased.

[Sequence Listings]

The invention claimed is:

1. A method for producing a cellulose degradation product, the method comprising:
generating the cellulose degradation product by bringing a material containing cellulose into contact with a thermostable cellobiohydrolase, having a cellulose-binding motif domain comprising: (A1) a polypeptide consisting of the amino acid sequence of SEQ ID NO: 1, and having a cellulose-binding function, and also having a cellobiohydrolase catalytic domain comprising: (A2) a polypeptide consisting of a partial sequence from a leucine residue at position 164 to a proline residue at position 590 of the amino acid sequence of SEQ ID NO: 3, wherein the thermostable cellobiohydrolase exhibits hydrolysis activity against a substrate of phosphoric acid swollen Avicel at least under conditions of 95° C. and pH 5.5 and
isolating the cellulose degradation product produced.

* * * * *

```
SEQUENCE LISTING

<160> NUMBER OF SEQ ID NOS: 14

<210> SEQ ID NO 1
<211> LENGTH: 102
<212> TYPE: PRT
<213> ORGANISM: Unknown
<220> FEATURE:
<223> OTHER INFORMATION: CBM of AR19G-166c4A-19-2

<400> SEQUENCE: 1

Cys Gln Val Ser Tyr Thr Val Ala Asn Gln Trp Pro Gly Gly Ala Thr
1               5                   10                  15

Val Asn Val Thr Ile Thr Asn Thr Ser Ser Pro Ile Asn Gly Trp
            20                  25                  30
```

-continued

```
Thr Leu Glu Trp Asp Phe Pro Asn Pro Ser Gln Gln Ile Thr Asn Leu
         35                  40                  45

Trp Asn Gly Ser Tyr Ser Gln Thr Gly Gln His Val Thr Val Thr Asn
 50                  55                  60

Ala Ala Trp Asn Gly Thr Ile Pro Ala Gly Ser Ser Val Thr Phe Gly
 65                  70                  75                  80

Phe Asn Met Ser Trp Ser Gly Ser Asn Pro Ala Pro Ser Ser Phe Thr
                 85                  90                  95

Leu Asn Gly Gln Pro Cys
            100
```

<210> SEQ ID NO 2
<211> LENGTH: 306
<212> TYPE: DNA
<213> ORGANISM: Unknown
<220> FEATURE:
<223> OTHER INFORMATION: CBM of AR19G-166c4A-19-2

<400> SEQUENCE: 2

```
tgccaggtgt cctacacggt agccaaccag tggcccggcg cgccaccgt gaacgtgaca      60
attaccaaca ccaccagcag ccccatcaac ggctggacgc tggaatggga cttccccaac    120
cccagccagc agatcaccaa cctctggaac ggctcctact cccaaaccgg acagcacgtg    180
acagtgacca tgccgcctg gaacggaaca atcccagccg gcagctccgt aaccttcgga    240
ttcaacatga gctggagcgg atcgaacccg gcgcccagca gcttcaccct gaacggacaa    300
ccgtgc                                                              306
```

<210> SEQ ID NO 3
<211> LENGTH: 590
<212> TYPE: PRT
<213> ORGANISM: Unknown
<220> FEATURE:
<223> OTHER INFORMATION: AR19G-166c4A-19-2

<400> SEQUENCE: 3

```
Ala Cys Gln Val Ser Tyr Thr Val Ala Asn Gln Trp Pro Gly Gly Ala
 1               5                  10                  15

Thr Val Asn Val Thr Ile Thr Asn Thr Thr Ser Ser Pro Ile Asn Gly
                 20                  25                  30

Trp Thr Leu Glu Trp Asp Phe Pro Asn Pro Ser Gln Gln Ile Thr Asn
             35                  40                  45

Leu Trp Asn Gly Ser Tyr Ser Gln Thr Gly Gln His Val Thr Val Thr
 50                  55                  60

Asn Ala Ala Trp Asn Gly Thr Ile Pro Ala Gly Ser Ser Val Thr Phe
 65                  70                  75                  80

Gly Phe Asn Met Ser Trp Ser Gly Ser Asn Pro Ala Pro Ser Ser Phe
                 85                  90                  95

Thr Leu Asn Gly Gln Pro Cys Gly Gly Thr Ala Gly Gly Pro Gln
            100                 105                 110

Pro Thr Pro Thr Pro Thr Arg Thr Pro Thr Pro Ala Ala Pro Thr Ala
            115                 120                 125

Thr Pro Thr Pro Val Ala Pro Thr Ala Thr Pro Thr Arg Thr Pro Thr
            130                 135                 140

Pro Thr Leu Thr Ser Thr Pro Gly Pro Thr Pro Thr Pro Pro Ser
145                 150                 155                 160

Gly Thr His Leu Asp Asn Pro Phe Ile Gly Ala Ile Gly Tyr Val Asn
            165                 170                 175
```

-continued

Pro Asp Trp Ala Thr Asn Val Ile Ser Gln Ala Asn Gln Thr Ala Asp
            180                 185                 190

Pro Thr Leu Ala Ala Gln Met Arg Lys Val Ala Thr Tyr Ser Thr Ala
        195                 200                 205

Val Trp Leu Asp Arg Ile Ala Ala Ile Thr Ala Gly Arg Gly Leu Arg
    210                 215                 220

Gly His Leu Asp Glu Ala Leu Arg Gln Met Gln Gln Ala Gly Gln Pro
225                 230                 235                 240

Val Val Ile Thr Leu Val Ile Tyr Asp Leu Pro Asn Arg Asp Cys Ser
                245                 250                 255

Ala Ala Ala Ser Asn Gly Glu Leu Leu Val Ala Gln Asn Gly Leu Ala
            260                 265                 270

Arg Tyr Lys Ala Glu Phe Ile Asp Pro Ile Val Ala Ile Leu Ser Asp
        275                 280                 285

Pro Arg Tyr Ala Gly Leu Arg Ile Val Thr Ile Ile Glu Pro Asp Ser
    290                 295                 300

Leu Pro Asn Leu Val Thr Asn Leu Ser Ile Pro Ala Cys Ala Glu Ala
305                 310                 315                 320

Gln Asn Ala Tyr Ile Glu Gly Ile Arg Tyr Ala Val Asn Arg Leu Arg
                325                 330                 335

Thr Ile Pro Asn Val Tyr Ile Tyr Leu Asp Ile Ala His Ser Gly Trp
            340                 345                 350

Leu Gly Trp Asp Asn Asn Phe Asn Gly Ala Val Asn Leu Tyr Thr Gln
        355                 360                 365

Val Val Gln Gly Met Asp Gln Gly Phe Asn Ser Ile Asp Gly Phe Ile
    370                 375                 380

Thr Asn Val Ala Asn Tyr Thr Pro Leu Glu Glu Pro Tyr Leu Pro Asp
385                 390                 395                 400

Pro Asn Leu Thr Ile Ala Gly Gln Pro Val Arg Ser Ala Ser Phe Tyr
                405                 410                 415

Glu Trp Asn Pro Tyr Phe Asp Glu Leu Asp Tyr Ala Leu Ala Leu Arg
            420                 425                 430

Asn Ala Phe Ile Gly Arg Gly Phe Pro Ser Thr Ile Gly Met Leu Ile
        435                 440                 445

Asp Thr Ser Arg Asn Gly Trp Gly Gly Cys Ser Tyr Gly Gln Cys Arg
    450                 455                 460

Pro Thr Gly Pro Ser Ser Asp Thr Ser Ser Val Asn Ala Tyr Val Asp
465                 470                 475                 480

Gly Ser Arg Val Asp Arg Arg Tyr His Arg Gly Asn Trp Cys Asn Gln
                485                 490                 495

Ala Gly Gly Ile Gly Glu Arg Pro Gln Ala Ala Pro Arg Ser Gly Ile
            500                 505                 510

Asp Ala Tyr Val Trp Val Lys Pro Pro Gly Glu Ser Asp Gly Val Ser
        515                 520                 525

Gln Pro Gly Ile Val Asp Pro Asp Pro Asn Lys Lys Phe Asp Pro
    530                 535                 540

Met Cys Asp Pro Asn Gly Gln Ser Arg Tyr Asn Ser Ala Tyr Pro Thr
545                 550                 555                 560

Gly Ala Leu Pro Asn Ala Pro His Ala Gly Arg Trp Phe Pro Gln Gln
                565                 570                 575

Phe Glu Ile Leu Val Arg Asn Ala Tyr Pro Pro Ile Gln Pro
            580                 585                 590

<210> SEQ ID NO 4
<211> LENGTH: 1773
<212> TYPE: DNA
<213> ORGANISM: Unknown
<220> FEATURE:
<223> OTHER INFORMATION: AR19G-166c4A-19-2

<400> SEQUENCE: 4

```
gcctgccagg tgtcctacac ggtagccaac cagtggcccg gcggcgccac cgtgaacgtg      60
acaattacca acaccaccag cagccccatc aacggctgga cgctggaatg ggacttcccc     120
aaccccagcc agcagatcac caacctctgg aacggctcct actcccaaac cggacagcac     180
gtgacagtga ccaatgccgc ctggaacgga acaatcccag ccggcagctc cgtaaccttc     240
ggattcaaca tgagctggag cggatcgaac ccggcgccca gcagcttcac cctgaacgga     300
caaccgtgcg gcggcaccgc cggcggtggc ccccagccca ccccaccccc cacgcgcacg     360
cccacaccgg cggcacctac cgccaccccc acgccggtgg cgcccaccgc caccccccac     420
cgcacgccca ccgacacact cacctctacg ccggggccta caccaacgcc accccttca     480
ggaacccatt tggacaatcc attcatcgga gccatcggat acgtgaatcc ggactgggca     540
accaatgtga tcagccaagc gaaccaaacg gctgatccaa ccttggcggc tcaaatgcgt     600
aaggtggcca cctactccac agctgtctgg ttggatcgta tcgccgccat caccgctggc     660
cgcggattgc gcgggcattt ggatgaagca ctacgccaaa tgcagcaagc tggccagccg     720
gttgtgatca ccccttgtga tctatgatctg ccaaatcgag attgctctgc tgctgcctcc     780
aatggcgaat tactggtcgc ccagaatgga ctggcccgct acaaagcgga gttcatcgat     840
cccatcgtag ccattctctc agatcccga tatgccgggc tacgcatcgt caccatcatc     900
gaaccggact ccttacccaa cctggtcacg aacctcagca tcccggcatg cgcagaagct     960
cagaatgcat atatcgaagg gatccgctat gcggtgaacc ggctgcggac aattcccaac    1020
gtctacatct atctggatat cgcccactca ggctggttgg gctgggataa taactttaat    1080
ggggcagtaa atctctacac ccaagttgtg caaggaatgg atcaagggtt taacagtatc    1140
gatggattca tcaccaacgt tgccaactat accccctcg aagaacccta tttgcccgat    1200
cccaacctga ccatcgctgg gcaacccgtt cgctctgcca gcttctacga atggaaccccc    1260
tactttgatg agctggatta cgctctggct ctgcgcaacg ctttatcgg acgaggcttc    1320
cccagcacca ttgggatgct catcgatacc agccgaaacg ggtggggcgg atgcagctat    1380
gggcaatgca ggcccacggg tcccagttca gataccagca gcgtgaatgc ctacgtggac    1440
ggctcgcgag tagaccgacg ctatcatcgg ggcaactggt gtaaccaggc gggtgggatc    1500
ggcgagcgcc ctcaggccgc accgcggtcc ggtatcgacg cctacgtgtg ggtgaaacca    1560
cctggggagt ccgatggggt cagccaaccc gggatcgtcg atcccgacga tcccaacaag    1620
aagttcgatc ctatgtgtga tcccaacgga cagagccggt ataactccgc atcccaact    1680
ggggctctgc ccaacgcgcc ccacgctggg cggtggttcc cgcagcagtt cgaaatcctg    1740
gtgcggaacg cctatccgcc gatccaaccc taa                                 1773
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer.

<400> SEQUENCE: 5
gcctgccagg tgtcctac                                                     18

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer.

<400> SEQUENCE: 6
ttagggttgg atcggcggat ag                                                22

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer.

<400> SEQUENCE: 7
gtgatggcct gccaggtgtc ctac                                              24

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 8
atgcagagct cttagggttg gatcggcgga tag                                    33

<210> SEQ ID NO 9
<211> LENGTH: 480
<212> TYPE: PRT
<213> ORGANISM: Microbispora sp.

<400> SEQUENCE: 9

```
Met Ser Ala Ala Ala Val Ala Thr Leu Val Thr Ala Ala Ala Gly Val
1               5                   10                  15

Ala Gly Thr His Ala Ala Ser Ala Ala Ala Ala Gly Cys Gln Val Thr
            20                  25                  30

Tyr Thr Val Thr Asn Gln Trp Pro Gly Gly Phe Gly Thr Asn Val Thr
        35                  40                  45

Ile Ser Asn Leu Gly Asp Pro Val Asn Gly Trp Arg Leu Thr Trp Ser
    50                  55                  60

Phe Pro Ala Gly Gln Thr Val Thr Gln Leu Trp Asn Gly Thr Tyr Thr
65                  70                  75                  80

Gln Ser Gly Ser Gln Val Thr Val Thr Asn Ala Ser Tyr Asn Ala Thr
                85                  90                  95

Ile Pro Thr Gly Gly Ser Thr Asn Phe Gly Phe Asn Gly Ser Trp Asn
            100                 105                 110

Gly Ser Asn Pro Ala Pro Ser Ser Phe Ala Leu Asn Gly Val Thr Cys
        115                 120                 125

Thr Gly Gly Val Thr Ser Pro Thr Pro Thr Pro Thr Pro Thr Pro Thr
    130                 135                 140

Pro Thr Pro Thr Pro Thr Pro Thr Pro Thr Pro Ser Pro Ser Pro Ser
145                 150                 155                 160
```

Pro Ser Thr Arg Gln Pro Cys Asp Ile Tyr Ala Ser Gly Gly Thr Pro
            165                 170                 175

Cys Val Ala Ala His Ser Thr Thr Arg Ala Leu Tyr Ala Ala Tyr Thr
        180                 185                 190

Gly Pro Leu Tyr Gln Val Arg Arg Ser Ser Asp Asn Thr Thr Arg Asp
        195                 200                 205

Ile Gly Val Leu Ser Ala Gly Val Ala Asp Ser Ala Ala Gln Asp
    210                 215                 220

Ser Phe Cys Ala Asn Thr Asn Cys Val Ile Thr Val Ile Tyr Asp Gln
225                 230                 235                 240

Ser Gly Arg Asn Asn Arg Leu Thr Gln Ala Pro Pro Gly Gly Phe Ala
                245                 250                 255

Gly Pro Ala Ala Gly Gly Tyr Asp Asn Leu Ala Asp Ala Lys Ala Ala
            260                 265                 270

Pro Thr Thr Val Gly Gly His Lys Ala Tyr Gly Val Tyr Val Ala Ala
        275                 280                 285

Gly Thr Gly Tyr Arg Asn Asn Ala Thr Asn Gly Val Ala Lys Gly Asp
        290                 295                 300

Gln Pro Glu Gly Met Tyr Ala Ile Phe Asp Gly Thr His Tyr Asn Gly
305                 310                 315                 320

Gly Cys Cys Phe Asp Tyr Gly Asn Ala Glu Thr Asn Ser Arg Asp Asn
                325                 330                 335

Gly Asn Gly Thr Met Glu Ala Ile Tyr Phe Gly Asn Ile Lys Val Trp
            340                 345                 350

Gly Tyr Gly Thr Gly Asn Gly Pro Trp Ile Met Ala Asp Leu Glu Asn
        355                 360                 365

Gly Leu Phe Ser Gly Val Asn Ala Gly Tyr Asn Ala Asn Asp Pro Thr
    370                 375                 380

Val Asn Tyr Arg Tyr Leu Thr Ala Ile Ile Lys Gly Glu Ser Asn His
385                 390                 395                 400

Trp Ala Ile Arg Gly Gly Asn Ala Gln Ser Gly Gly Leu Ser Thr Phe
                405                 410                 415

Tyr Asp Gly Lys Arg Pro Asn Val Ser Gly Tyr Asn Pro Met Lys Lys
            420                 425                 430

Glu Gly Ala Ile Ile Leu Gly Ile Gly Gly Asp Asn Ser His Gly Ser
        435                 440                 445

Ala Gly Thr Phe Tyr Glu Gly Val Met Thr Ser Gly Tyr Pro Ser Asp
    450                 455                 460

Ala Thr Glu Ser Ala Val Gln Ala Asn Ile Val Ala Ala Gly Tyr Arg
465                 470                 475                 480

<210> SEQ ID NO 10
<211> LENGTH: 427
<212> TYPE: PRT
<213> ORGANISM: Unknown
<220> FEATURE:
<223> OTHER INFORMATION: AR19G-166-QA

<400> SEQUENCE: 10

Leu Asp Asn Pro Phe Ile Gly Ala Ile Gly Tyr Val Asn Pro Asp Trp
1               5                   10                  15

Ala Thr Asn Val Ile Ser Gln Ala Asn Gln Thr Ala Asp Pro Thr Leu
            20                  25                  30

Ala Ala Gln Met Arg Lys Val Ala Thr Tyr Ser Thr Ala Val Trp Leu
        35                  40                  45

-continued

Asp Arg Ile Ala Ala Ile Thr Ala Gly Arg Gly Leu Arg Gly His Leu
        50                  55                  60
Asp Glu Ala Leu Arg Gln Met Gln Gln Ala Gly Gln Pro Val Val Ile
 65                  70                  75                  80
Thr Leu Val Ile Tyr Asp Leu Pro Asn Arg Asp Cys Ser Ala Ala Ala
                 85                  90                  95
Ser Asn Gly Glu Leu Leu Val Ala Gln Asn Gly Leu Ala Arg Tyr Lys
            100                 105                 110
Ala Glu Phe Ile Asp Pro Ile Val Ala Ile Leu Ser Asp Pro Arg Tyr
            115                 120                 125
Ala Gly Leu Arg Ile Val Thr Ile Ile Glu Pro Asp Ser Leu Pro Asn
        130                 135                 140
Leu Val Thr Asn Leu Ser Ile Pro Ala Cys Ala Glu Ala Gln Asn Ala
145                 150                 155                 160
Tyr Ile Glu Gly Ile Arg Tyr Ala Val Asn Arg Leu Arg Thr Ile Pro
                165                 170                 175
Asn Val Tyr Ile Tyr Leu Asp Ile Ala His Ser Gly Trp Leu Gly Trp
            180                 185                 190
Asp Asn Asn Phe Asn Gly Ala Val Asn Leu Tyr Thr Gln Val Val Gln
        195                 200                 205
Gly Met Asp Gln Gly Phe Asn Ser Ile Asp Gly Phe Ile Thr Asn Val
    210                 215                 220
Ala Asn Tyr Thr Pro Leu Glu Glu Pro Tyr Leu Pro Asp Pro Asn Leu
225                 230                 235                 240
Thr Ile Ala Gly Gln Pro Val Arg Ser Ala Ser Phe Tyr Glu Trp Asn
                245                 250                 255
Pro Tyr Phe Asp Glu Leu Asp Tyr Ala Leu Ala Leu Arg Asn Ala Phe
            260                 265                 270
Ile Gly Arg Gly Phe Pro Ser Thr Ile Gly Met Leu Ile Asp Thr Ser
        275                 280                 285
Arg Asn Gly Trp Gly Gly Cys Ser Tyr Gly Gln Cys Arg Pro Thr Gly
    290                 295                 300
Pro Ser Ser Asp Thr Ser Ser Val Asn Ala Tyr Val Asp Gly Ser Arg
305                 310                 315                 320
Val Asp Arg Arg Tyr His Arg Gly Asn Trp Cys Asn Gln Ala Gly Gly
                325                 330                 335
Ile Gly Glu Arg Pro Gln Ala Ala Pro Arg Ser Gly Ile Asp Ala Tyr
            340                 345                 350
Val Trp Val Lys Pro Pro Gly Glu Ser Asp Gly Val Ser Gln Pro Gly
        355                 360                 365
Ile Val Asp Pro Asp Pro Asn Lys Lys Phe Asp Pro Met Cys Asp
        370                 375                 380
Pro Asn Gly Gln Ser Arg Tyr Asn Ser Ala Tyr Pro Thr Gly Ala Leu
385                 390                 395                 400
Pro Asn Ala Pro His Ala Gly Arg Trp Phe Gln Gln Phe Glu Ile
                405                 410                 415
Leu Val Arg Asn Ala Tyr Pro Pro Ile Gln Pro
            420                 425

<210> SEQ ID NO 11
<211> LENGTH: 590
<212> TYPE: PRT
<213> ORGANISM: Unknown
<220> FEATURE:
<223> OTHER INFORMATION: AR19G-166c4A-19-2-1

<400> SEQUENCE: 11

```
Ala Cys Gln Val Ser Tyr Thr Val Ala Asn Gln Trp Pro Gly Gly Ala
1               5                   10                  15

Thr Val Asn Val Thr Ile Thr Asn Thr Thr Ser Ser Pro Ile Asn Gly
            20                  25                  30

Trp Thr Leu Glu Trp Asp Phe Pro Asn Pro Ser Gln Gln Ile Thr Asn
        35                  40                  45

Leu Trp Asn Gly Ser Tyr Ser Gln Thr Gly His Val Thr Val Thr
    50                  55                  60

Asn Ala Ala Trp Asn Gly Thr Ile Pro Ala Gly Ser Ser Val Thr Phe
65                  70                  75                  80

Gly Phe Asn Met Ser Trp Ser Gly Ser Asn Pro Ala Pro Ser Ser Phe
                85                  90                  95

Thr Leu Asn Gly Gln Pro Cys Gly Gly Thr Ala Gly Gly Pro Gln
            100                 105                 110

Pro Thr Pro Thr Pro Thr Arg Thr Pro Thr Pro Ala Ala Pro Thr Ala
                115                 120                 125

Thr Pro Thr Pro Val Ala Pro Thr Ala Thr Pro Thr Arg Thr Pro Thr
            130                 135                 140

Pro Thr Leu Thr Ser Thr Pro Gly Pro Thr Pro Thr Pro Pro Ser
145                 150                 155                 160

Gly Thr His Leu Asp Asn Pro Phe Ile Gly Ala Ile Gly Tyr Val Asn
                165                 170                 175

Pro Asp Trp Ala Thr Asn Val Ile Ser Gln Ala Asn Gln Thr Ala Asp
            180                 185                 190

Pro Thr Leu Ala Ala Gln Met Arg Lys Val Ala Thr Tyr Ser Thr Ala
        195                 200                 205

Val Trp Leu Asp Arg Ile Ala Ala Ile Thr Ala Gly Arg Gly Leu Arg
    210                 215                 220

Gly His Leu Asp Glu Ala Leu Arg Gln Met Gln Gln Ala Gly Gln Pro
225                 230                 235                 240

Val Val Ile Thr Leu Val Ile Tyr Asp Leu Pro Asn Arg Asp Cys Ser
                245                 250                 255

Ala Ala Ala Ser Asn Gly Glu Leu Leu Val Ala Gln Asn Gly Leu Ala
            260                 265                 270

Arg Tyr Lys Ala Glu Phe Ile Asp Pro Ile Val Ala Ile Leu Ser Asp
        275                 280                 285

Pro Arg Tyr Ala Gly Leu Arg Ile Val Thr Ile Ile Glu Pro Asp Ser
    290                 295                 300

Leu Pro Asn Leu Val Thr Asn Leu Ser Ile Pro Ala Cys Ala Glu Ala
305                 310                 315                 320

Gln Asn Ala Tyr Ile Glu Gly Ile Arg Tyr Ala Val Asn Arg Leu Arg
                325                 330                 335

Thr Ile Pro Asn Val Tyr Ile Tyr Leu Asp Ile Ala His Ser Gly Trp
            340                 345                 350

Leu Gly Trp Asp Asn Asn Phe Asn Gly Ala Val Asn Leu Tyr Thr Gln
        355                 360                 365

Val Val Gln Gly Met Asp Gln Gly Phe Asn Ser Ile Asp Gly Phe Ile
    370                 375                 380

Thr Asn Val Ala Asn Tyr Thr Pro Leu Glu Glu Pro Tyr Leu Pro Asp
385                 390                 395                 400

Pro Asn Leu Thr Ile Ala Gly Gln Pro Val Arg Ser Ala Ser Phe Tyr
                405                 410                 415
```

Glu Trp Asn Pro Tyr Phe Asp Glu Leu Asp Tyr Ala Leu Ala Leu Arg
            420                 425                 430

Asn Ala Phe Ile Gly Arg Gly Phe Pro Ser Thr Ile Gly Met Leu Ile
        435                 440                 445

Asp Thr Ser Arg Asn Gly Trp Gly Gly Cys Ser Tyr Gly Arg Cys Arg
    450                 455                 460

Pro Thr Gly Pro Ser Ser Asp Thr Ser Ser Val Asn Ala Tyr Val Asp
465                 470                 475                 480

Gly Ser Arg Val Asp Arg Arg Tyr His Arg Gly Asn Trp Cys Asn Gln
                485                 490                 495

Ala Gly Gly Ile Gly Glu Arg Pro Gln Ala Ala Pro Arg Ser Gly Ile
            500                 505                 510

Asp Ala Tyr Val Trp Val Lys Pro Pro Gly Glu Ser Asp Gly Val Ser
        515                 520                 525

Gln Pro Gly Ile Val Asp Pro Asp Pro Asn Lys Lys Phe Asp Pro
    530                 535                 540

Met Cys Asp Pro Asn Gly Gln Ser Arg Tyr Asn Ser Ala Tyr Pro Thr
545                 550                 555                 560

Gly Ala Leu Pro Asn Ala Pro His Ala Gly Arg Trp Phe Pro Gln Gln
                565                 570                 575

Phe Glu Ile Leu Val Arg Asn Ala Tyr Pro Pro Ile Gln Pro
            580                 585                 590

<210> SEQ ID NO 12
<211> LENGTH: 1773
<212> TYPE: DNA
<213> ORGANISM: Unknown
<220> FEATURE:
<223> OTHER INFORMATION: AR19G-166c4A-19-2-1

<400> SEQUENCE: 12

| | | | | | | |
|---|---|---|---|---|---|---|
| gcctgccagg | tgtcctacac | ggtagccaac | cagtggcccg | gcggcgccac | cgtgaacgtg | 60 |
| acaattacca | acaccaccag | cagccccatc | aacggctgga | cgctggaatg | ggacttcccc | 120 |
| aaccccagcc | agcagatcac | caacctctgg | aacggctcct | actcccaaac | cggacagcac | 180 |
| gtgacagtga | ccaatgccgc | ctggaacgga | caatcccag | ccggcagctc | cgtaaccttc | 240 |
| ggattcaaca | tgagctggag | cggatcgaac | ccggcgccca | gcagcttcac | cctgaacgga | 300 |
| caaccgtgcg | gcggcaccgc | cggcggtggc | ccccagccca | cccccacccc | cacgcgcacg | 360 |
| cccacaccgg | cggcacctac | cgccacccc | acgccggtgg | cgcccaccgc | cacccccacc | 420 |
| cgcacgccca | caccgacact | cacctctacg | ccggggccta | caccaacgcc | accccttca | 480 |
| ggaacccatt | tggacaatcc | attcatcgga | gccatcggat | acgtgaatcc | ggactgggca | 540 |
| accaatgtga | tcagccaagc | gaaccaaacg | gctgatccaa | ccttggcggc | tcaaatgcgt | 600 |
| aaggtggcca | cctactccac | agctgtctgg | ttggatcgta | tcgccgccat | caccgctggc | 660 |
| cgcggattgc | gcgggcattt | ggatgaagca | ctacgccaaa | tgcagcaagc | tggccagccg | 720 |
| gttgtgatca | cccttgtgat | ctatgatctg | ccaaatcgag | attgctctgc | tgctgcctcc | 780 |
| aatggcgaat | actggtcgc | ccagaatgga | ctggcccgct | acaaagcgga | gttcatcgat | 840 |
| cccatcgtag | ccattctctc | agatccccga | tatgccgggc | tacgcatcgt | caccatcatc | 900 |
| gaaccggact | ccttacccaa | cctggtcacg | aacctcagca | tcccggcatg | cgcagaagct | 960 |
| cagaatgcat | atatcgaagg | gatccgctat | gcggtgaacc | ggctgcggac | aattcccaac | 1020 |
| gtctacatct | atctggatat | cgcccactca | ggctggttgg | gctgggataa | taactttaat | 1080 |

```
ggggcagtaa atctctacac ccaagttgtg caaggaatgg atcaagggtt taacagtatc    1140
gatggattca tcaccaacgt tgccaactat acccccctcg aagaacccta tttgcccgat    1200
cccaacctga ccatcgctgg gcaacccgtt cgctctgcca gcttctacga atggaacccc    1260
tactttgatg agctggatta cgctctggct ctgcgcaacg cttttatcgg acgaggcttc    1320
cccagcacca ttgggatgct catcgatacc agccgaaacg ggtggggcgg atgcagctat    1380
gggcgatgca ggcccacggg tcccagttca gataccagca gcgtgaatgc ctacgtggac    1440
ggctcgcgag tagaccgacg ctatcatcgg ggcaactggt gtaaccaggc gggtgggatc    1500
ggcgagcgcc ctcaggccgc accgcggtcc ggtatcgacg cctacgtgtg ggtgaaacca    1560
cctggggagt ccgatggggt cagccaaccc gggatcgtcg atcccgacga tcccaacaag    1620
aagttcgatc ctatgtgtga tcccaacgga cagagccggt ataactccgc atacccaact    1680
ggggctctgc ccaacgcgcc ccacgctggg cggtggttcc cgcagcagtt cgaaatcctg    1740
gtgcggaacg cctatccgcc gatccaaccc taa                                 1773

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 13
atgcagctat gggcgatgca ggcccacggg                                      30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 14
cccgtgggcc tgcatcgccc atagctgcat                                      30
```